US010190097B2

(12) United States Patent
Soo et al.

(10) Patent No.: US 10,190,097 B2
(45) Date of Patent: Jan. 29, 2019

(54) METHOD AND COMPOSITION FOR INDUCING HUMAN PLURIPOTENT STEM CELLS

(71) Applicant: The Regents of the University of California, Oakland, CA (US)

(72) Inventors: B. Chia Soo, Beverly Hills, CA (US); Kang Ting, Beverly Hills, CA (US); Zhong Zheng, Van Nuys, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/383,752

(22) Filed: Dec. 19, 2016

(65) Prior Publication Data

US 2017/0159021 A1 Jun. 8, 2017

Related U.S. Application Data

(62) Division of application No. 14/353,284, filed as application No. PCT/US2012/061389 on Oct. 22, 2012, now Pat. No. 9,549,954.

(60) Provisional application No. 61/550,348, filed on Oct. 21, 2011.

(51) Int. Cl.

| | |
|---|---|
| ***C12N 5/02*** | (2006.01) |
| ***C12N 5/071*** | (2010.01) |
| ***C07K 1/00*** | (2006.01) |
| ***C12N 5/074*** | (2010.01) |
| ***A61K 35/12*** | (2015.01) |
| ***A61K 38/18*** | (2006.01) |
| ***A61K 35/33*** | (2015.01) |
| ***A61K 38/17*** | (2006.01) |
| *C12N 5/07* | (2010.01) |
| *C07K 14/435* | (2006.01) |

(52) U.S. Cl.

CPC ............ *C12N 5/0696* (2013.01); *A61K 35/12* (2013.01); *A61K 35/33* (2013.01); *A61K 38/1709* (2013.01); *A61K 38/18* (2013.01); *C07K 14/435* (2013.01); *C12N 5/06* (2013.01); *C12N 2501/15* (2013.01); *C12N 2501/998* (2013.01); *C12N 2506/00* (2013.01); *C12N 2506/13* (2013.01); *C12N 2506/1307* (2013.01)

(58) Field of Classification Search

CPC ................ C12N 5/06; C12N 2501/998; C12N 2506/1307; C12N 2506/00; C07K 14/435

USPC ................................. 435/366, 377; 530/350

See application file for complete search history.

(56) References Cited

U.S. PATENT DOCUMENTS

| | | | | |
|---|---|---|---|---|
| 9,549,954 | B2 * | 1/2017 | Soo ....................... | A61K 35/12 |
| 2010/0330182 | A1 | 12/2010 | Young et al. | |
| 2011/0244566 | A1 | 10/2011 | Wu et al. | |
| 2013/0078223 | A1 | 3/2013 | Ting et al. | |
| 2014/0369971 | A1 | 12/2014 | Soo et al. | |
| 2017/0159022 | A1 | 6/2017 | Soo | |

FOREIGN PATENT DOCUMENTS

| | | | |
|---|---|---|---|
| WO | 2010033906 | A2 | 3/2010 |
| WO | 2011056971 | A2 | 5/2011 |
| WO | 2011143400 | A2 | 11/2011 |
| WO | 2013059829 | | 4/2013 |

OTHER PUBLICATIONS

Abeyta, M. J. et al., "Unique gene expression signatures of independently-derived human embryonic stem cell lines", Human Molecular Genetics, vol. 13, No. 6, 2004, pp. 601-608.

Alenzi, F. Q. B. and Bahkali, A. H. "Stem cells: Biology and clinical potential", African Journal of Biotechnology, vol. 10, No. 86, 2011, pp. 19929-19940.

Allegrucci, C. and Young. L. E. "Differences between human embryonic stem cell lines", Human Reproduction Update, vol. Advance Access published Aug. 26, 2006, pp. 1-18.

Bellin, M. et al., "Induced pluripotent stem cells: the new patient?", Nature Reviews/Molecular Biology, vol. 13, 2012, pp. 713-726.

Bryan, P. N. and Orban, J. "Implications of protein fold switching", http://www.elsevierblogs.com/currentcomments/?p=962, pp. 1-4.

Chattopadhyay, A. et al., "Effect of single amino acid mutations in the conserved GDNQ motif of L protein of Rinderpest virus on RNA synthesis in vitro and in vivo", Virus Research, vol. 99, 2004, pp. 139-145.

Kolf, C. M. et al., "Biology of adult mesenchymal stem cells: regulation of niche, self-renewal and differentiation", Arthritis Research & Therapy, vol. 9, 2007, pp. 1-10.

Li, J. et al., "Advances in understanding the cell-types and approaches used for generating induced pluripotent stem cells", Journal of Hematology & Oncology, 7:50, 2014, pp. 1-18.

Pandey, Prativa, 2007, Abstracts, 59th Southeast regional Meeting of the American Chemical Society, Greenville, SC, United States, GEN-671, Publisher: American Chemical Society, Washington D.C.

Tomasinsig, L. and Zanetti, M. "THe Cathelicidins—Structure, Function and Evolution", Current Protein and Peptide Science, vol. 6, 2005, pp. 23-34.

Zhao, W. et al., "Embryonic Stem Cell Markers", Molecules, vol. 17, 2012, pp. 6196-6236.

International Search Report for International Application No. PCT/US2012/061389, dated Mar. 29, 2013.

(Continued)

*Primary Examiner* — Shin Lin Chen

(74) *Attorney, Agent, or Firm* — Taylor English Duma LLP

(57) ABSTRACT

The present invention provides a method of forming a fibromodulin (FMOD) reprogrammed (FReP) cell. The method comprises steps of treating a human cell with a cell culture medium comprising fibromodulin (FMOD) for a period ranging from a day to a month, and changing the cell culture medium regularly until a FMOD reprogrammed (FreP) cell forms; wherein the FreP cell expresses NANOG and does not form teratoma, and wherein the human cell is a fibroblastic cell.

3 Claims, 9 Drawing Sheets

Specification includes a Sequence Listing.

(56) References Cited

OTHER PUBLICATIONS

Written Opinion of the International Search Authority for International Application No. PCT/US2012/061389, dated Mar. 29, 2013.
International Preliminary Report of Patentability for International Application No. PCT/US2012/061389, dated Apr. 22, 2014.
Zheng, Z. et al., "Reprogramming of human fibroblasts into multipotent cells with a single ECM proteoglycan, fibromodulin", Biomaterials, vol. 33, 2012; pp. 5821-5831.
Soo, B. Chia; Advisory Action for U.S. Appl. No. 14/353,284, filed Apr. 21, 2014, dated Aug. 2, 2016, 3 pgs.
Soo, B. Chia; Final Office Action for U.S. Appl. No. 14/353,284, filed Apr. 21, 2014, dated Apr. 26, 2016, 12 pgs.
Soo, B. Chia; Issue Notification for U.S. Appl. No. 14/353,284, filed Apr. 21, 2014, dated Jan. 4, 2017, 1 pg.
Soo, B. Chia; Non-Final Office Action for U.S. Appl. No. 14/353,284, filed Apr. 21, 2014, dated Nov. 19, 2015, 23 pgs.
Soo, B. Chia; Notice of Allowance for U.S. Appl. No. 14/353,284, filed Apr. 21, 2014, dated Sep. 13, 2016, 9 pgs.
Soo, B. Chia; Restriction Requirement for U.S. Appl. No. 14/353,284, filed Apr. 21, 2014, dated Jul. 22, 2016, 3 gs.
Soo, B. Chia; Restriction Requirement for U.S. Appl. No. 14/353,284, filed Apr. 21, 2014, dated Aug. 6, 2015, 12 pgs.
Boo, B. Chia; Non-Final Office Action for U.S. Appl. No. 15/383,917, filed Dec. 19, 2016, dated Mar. 9, 2018, 24 pgs.
Soo, B. Chia; Restriction Requirement for U.S. Appl. No. 15/383,917, filed Dec. 19, 2016, dated Nov. 20, 2017, 6 pgs.

* cited by examiner

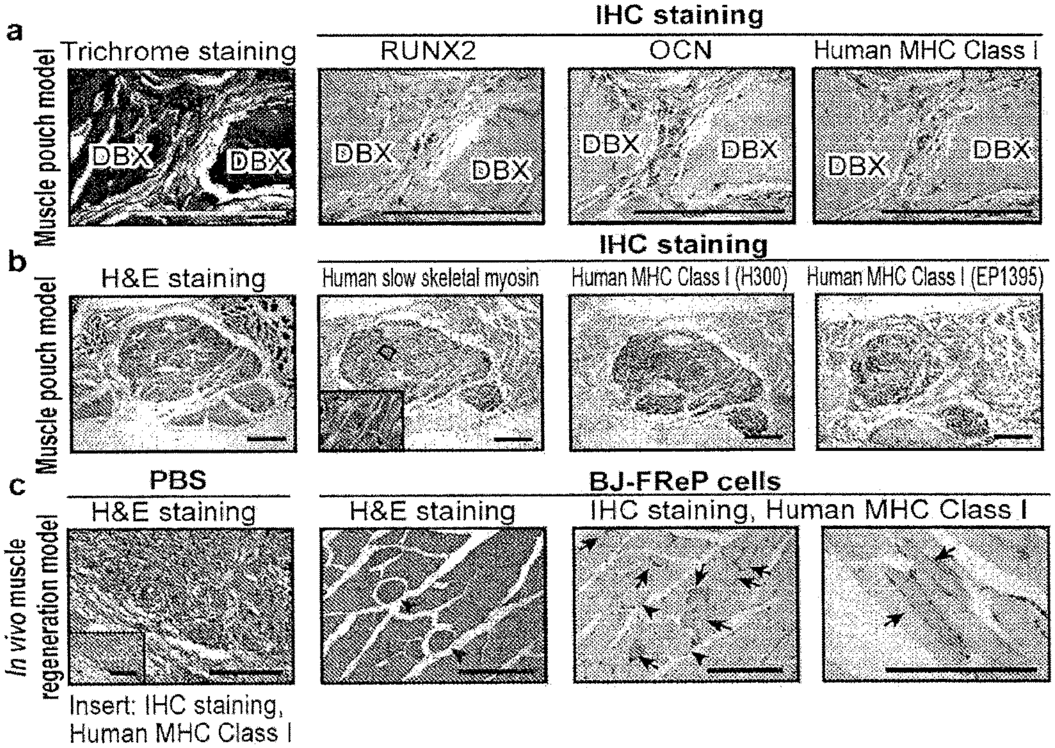

FIG. 5 a

*Teratoma Formation Analysis Report*

Service Detail

Cell type: undiffierentiated BJ-FReP
Feeder layer: MEF
Mouse type: Fox Chase SCID-beige, male, 6 week old
Cell concentration: 1-2 million cells/site
Injection date: December 12, 2010

| | Group #1 | Group #2 | Control |
|---|---|---|---|
| Injection sites | left/right kidney | left/right testis | left kidney left testis |
| Tumor harvested | no tumor | no tumor | kidney tumor testis tumor |
| Days post-injection | 73 | 94 | 68 |

Note: Control group was H9 ES cells.

b

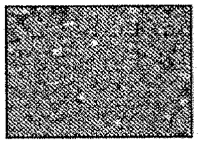

SCID-beige mice kidney injected with BJ-FReP cells, 73 days post injury. No tumor formation.

c

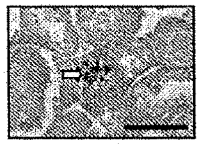

SCID-beige mice testis injected with BJ-FReP cells, 94 days post injury. No tumor formation, only calucified nodules remained.

FIG. 6

SEQUENCE LISTING

```
<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1

cggcttcctc ctcttcctct atac                                              24


<210> SEQ ID NO 2
<211> LENGTH: 26
<212> TYPE: DNA
<213> ORGANISM: Artificial Sequence
<220> FEATURE:
<223> OTHER INFORMATION: Synthetic primer

<400> SEQUENCE: 2

atcgatttca ctcatcttca cacgtc                                            26


<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3

ctgcagtgtg ggtttcgggc a                                                 21


<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4

cttgctgcag aagtgggtgg agga                                              24


<210> SEQ ID NO 5
<211> LENGTH: 22
<212> TYPE: DNA
<213> ORGANISM: Artificial Sequence
<220> FEATURE:
<223> OTHER INFORMATION: Synthetic primer

<400> SEQUENCE: 5

gagagaaaga aagggagaga ag                                                22


<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
```

-continued

```
gagagaggca aactggaatc                                                    20


<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7

tctgtggaga acgacatcca                                                    20


<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8

ctgtacgtct cagctctgtg a                                                  21


<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9

cagctggcgc acctcaagat g                                                  21


<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10

agggaagttg ggctcaggac tgg                                                23


<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11

atcagagatc aggaagcacc                                                    20


<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12

ggaacttcat ctgggtccat                                                    20


<210> SEQ ID NO 13
<211> LENGTH: 20
<212> TYPE: DNA
<213> ORGANISM: Artificial Sequence
```

<220> FEATURE:
<223> OTHER INFORMATION: Synthetic primer

<400> SEQUENCE: 13
acgggatgac caagtacagc 20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
acacactttg ggctggtagg 20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
ctccttcagg cagtgagagc 20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
gagatgcagt gtgctcgtgc 20

<210> SEQ ID NO 17
<211> LENGTH: 32
<212> TYPE: DNA
<213> ORGANISM: Artificial Sequence
<220> FEATURE:
<223> OTHER INFORMATION: Synthetic primer

<400> SEQUENCE: 17
atctggcacc acaccttcta caatgagctg cg 32

<210> SEQ ID NO 18
<211> LENGTH: 32
<212> TYPE: DNA
<213> ORGANISM: Artificial Sequence
<220> FEATURE:
<223> OTHER INFORMATION: Synthetic primer

<400> SEQUENCE: 18
cgtcatactc ctgcttgctg atccacatct gc 32

METHOD AND COMPOSITION FOR INDUCING HUMAN PLURIPOTENT STEM CELLS

CROSS-REFERENCE TO RELATED APPLICATIONS

This application is a divisional application of pending U.S. application Ser. No. 14/353,284, filed on Apr. 21, 2014, which claims priority to International Application No. PCT/US2012/061389, filed on Oct. 22, 2012, which in turn claims the benefit of U.S. Provisional Patent Application No. 61/550,348, filed Oct. 21, 2011. The teaching of these applications is incorporated herein by reference in its entirety.

STATEMENT OF GOVERNMENTAL SUPPORT

This invention was made with Government support under DE000422 and DE014649 awarded by the National Institutes of Health. The Government has certain rights in the invention.

FIELD OF THE INVENTION

The present invention relates generally to method and composition for cell pluripotency reprogramming.

BACKGROUND

Embryonic stem (ES) cells are pluripotent cells capable of both proliferation in a cell culture and differentiation towards a variety of lineage-restricted cell populations that exhibit multipotent properties (Odorico et al., Stem Cells 19: 193-204 (2001)). Because of these characteristics, ES cells, including human ES cells, can become very specific cell types that perform a variety of functions.

Generally, human ES cells are highly homogeneous, have a capacity for self-renewal and have an ability to differentiate into any functional cell in the body. Self-renewal can, under appropriate conditions, lead to a long-term proliferating capability with a potential for unlimited expansion in cell culture. In addition, if human ES cells differentiate in an undirected fashion, a heterogeneous population of cells is obtained that express markers for a plurality of different tissue types (WO 01/51616; and Shamblott et al., Proc. Natl. Acad. Sci. USA 98: 113 (2001)). These features make human ES cells a unique, homogeneous, starting population for the production of cells having therapeutic utility.

Human ES cells can be used to make a variety of differentiated cells types for scientific and commercial research use. At present, differentiated human cells of many types are not readily available and cannot be expanded in significant numbers in vitro culture. Human ES cells, however, can expand indefinitely in culture and can differentiate into many, if not all, the differentiated cell types of the human body. As such, culture techniques are being developed to induce human ES cells to differentiate into any number of specific cell types of the human body. The availability of human ES cells has opened the possibility that many differentiated human cells will become available in significant numbers for scientific and commercial research.

One difficulty in working with human ES cells is the development of conditions for the standardized culture of human ES cells without the use of animal products or products such as serum, which tend to vary from batch to batch. As such, the art desires culture conditions of human ES cell culture to be as defined as possible.

To work toward that desired goal, a set of culture conditions was recently described that permitted the long-term culture of undifferentiated human ES cells in defined conditions. Ludwig et al., Nat. Methods 3:637-646 (2006), incorporated herein by reference as if set forth in its entirety. Ludwig et al. described a medium, referred to herein as TeSR™ medium, for cultivation of human ES cells in which each constituent of the medium was fully disclosed and characterized. TeSR™ is therefore a fully defined and sufficient medium for human ES cell culture. TeSR™ has proven effective for use in the derivation of new human ES cell lines as well, which is an even more challenging constraint than the culture of undifferentiated human ES cells.

Human ES cells preferentially remain undifferentiated when grown in environments in which the cells are in direct contact with other cells or with physical structures in their environment. In other cellular environments, human ES cells begin to differentiate and become incapable of indefinite proliferation.

This is significant in the process of cloning an ES cell culture. As used herein, “cloning” means a process of initiating an ES cell culture from a starting culture, ideally, from a single ES cell or at least from very few ES cells. Culture conditions that permit clonal culture of undifferentiated ES cells may be the most demanding conditions of all of those required in normal ES cell culture and proliferation.

In spite of the progress in effectively culturing ES cells, several significant disadvantages with these methods still exist. For example, exposure to animal pathogens through MEF-conditioned medium or matrigel matrix is still a possibility. The major obstacle of the use of human ES cells in human therapy is that the originally described methods to propagate human ES cells involve culturing the human ES cells on a layer of feeder cells of non-human origin, and in the presence of nutrient serum of non-human origin. More recently, extensive research into improving culture systems for human ES cells has concentrated on the ability to grow ES cells under serum free/feeder-free conditions. For example, to ensure a feeder-free environment for the growth of human ES cells, a substitute system based on medium supplemented with serum replacement (SR), transforming growth factor β1 (TGF-β1), leukemia inhibitory factor (LIF), fibroblast growth factor (FGF) and a fibronectin matrix has also been tried (Amit et al (2004), Biol. Reprod. 70(3):837-45). As another example, despite substantial progress, most pluripotency reprogramming still requires at least one genome-integrated transcription factor, increasing risks of genome instability and tumor formation. A further example is formation of teratoma in the existing pluripotency reprogramming methods or systems.

Therefore, it is an objective of the present invention to provide a method of pluripotency reprogramming that reduces or minimizes the adverse effects associated with pluripotency reprogramming.

It is a further objective of the present invention to provide a pluripotency reprogrammed cell using a method of pluripotency reprogramming that reduces or minimizes the adverse effects associated with pluripotency reprogramming.

The embodiments below address the above identified issues and needs.

SUMMARY OF THE INVENTION

In one aspect of the present invention, it is provided a cell culture medium composition comprising fibromodulin (FMOD) or a derivative or fragment thereof, wherein the composition is effective for reprogramming a cell to form a FMOD reprogrammed (FReP) cell, wherein the FReP cell expresses NANOG and does not form teratoma in vivo.

In some embodiments of the cell culture medium, the FMOD has a concentration from about 200 nM to about 800 nM.

In some embodiments of the cell culture medium, optionally in combination with any or all of the above various embodiments, the cell is a human cell, mouse cell, and rat cell. In some embodiments, the cell can be a BJ fibroblast or primary adult normal human dermal fibroblast (NHDF).

In some embodiments of the cell culture medium, optionally in combination with any or all of the above various embodiments, reprogramming is without using a genome-integrated transcription factor.

In another aspect of the present invention, it is provided a method of pluripotency reprogramming, comprising:

treating a mammalian cell with a cell culture medium comprising fibromodulin (FMOD) or a derivative or fragment thereof for a period ranging from a day to a month, and changing the cell culture medium regularly until a FMOD reprogrammed pluripotent (FReP) cell forms;

wherein the FReP cell expresses NANOG and does not form teratoma in vivo.

In some embodiments of the method, optionally in combination with any or all of the above various embodiments, the FMOD has a concentration from about 200 nM to about 800 nM.

In some embodiments of the method, optionally in combination with any or all of the above various embodiments, the cell is a human cell, mouse cell, and rat cell. Examples of human cells include, e.g., BJ, MRC-5, HDF, keratinocytes, melanocytes, peripheral blood cells (e.g., CD34+), cord blood cells or even certain stem cells (e.g., adipose-derived stem cells, perivascular stem cells, neural stem cells).

In some embodiments of the method, optionally in combination with any or all of the above various embodiments, the cell is a BJ fibroblast or primary adult normal human dermal fibroblast (NHDF).

In some embodiments of the method, optionally in combination with any or all of the above various embodiments, the method is carried out without using a genome-integrated transcription factor.

In a further aspect of the present invention, it is provided a fibromodulin (FMOD) reprogrammed pluripotent (FReP) cell, which FReP cell is generated by a method comprising:

treating a mammalian cell with a cell culture medium for a period ranging from a day to a month, and changing the cell culture medium regularly until the FReP cell forms;

wherein the medium comprises fibromodulin (FMOD) or a derivative or fragment thereof, and wherein the FReP cell expresses NANOG and does not form teratoma in vivo.

In some embodiments of the FReP cell, optionally in combination with any or all of the above various embodiments, the FMOD has a concentration from about 200 nM to about 800 nM.

In some embodiments of the FReP cell, optionally in combination with any or all of the above various embodiments, the cell is a human cell, mouse cell, and rat cell. Examples of human cells include, e.g., BJ, MRC-5, NHDF, keratinocytes, melanocytes, peripheral blood cells (e.g., CD34+), cord blood cells or even certain stem cells (e.g., adipose-derived stem cells, perivascular stem cells, neural stem cells).

In some embodiments of the FReP cell, optionally in combination with any or all of the above various embodiments, the mammalian cell is a BJ fibroblast or primary adult normal human dermal fibroblast (HDF).

In another aspect of the present invention, it is provided a method of treating a disorder in a mammal, which method comprising administering to the mammal a FReP cell disclosed herein above and/or below.

In some embodiments of the method, optionally in combination with any or all of the above various embodiments, the mammal is a human being.

In some embodiments of the method, optionally in combination with any or all of the above various embodiments, the disorder is a neurodegenerative disorder.

In some embodiments of the method, optionally in combination with any or all of the above various embodiments, the disorder is a central nervous system (CNS) disease, cardiovascular disease, blood diseases, Crohn's disease, bone disease, muscle disease, or chondrocyte disease.

In some embodiments of the method, optionally in combination with any or all of the above various embodiments, the disorder is a retina disease, a trauma and injury to a tissue, a skeletal disorder, an organ disease or an injury to skin, muscle, cartilage, tendon, peripheral nerve, spinal cord, blood vessels, or bone.

In a further aspect of the present invention, it is provided a supernatant, comprising a cell culture medium disclosed above or below.

In some embodiments of the supernatant, the supernatant can be included in a composition. In some embodiments, such composition can be, for example, a pharmaceutical or cosmetic composition.

In a further aspect of the present invention, it is provided a method of treating or ameliorate a disorder, comprising administering to a mammalian subject a supernatant or a composition disclosed above or below.

In further aspect of the present invention, it is provided a method or inhibiting tumor growth, comprising adding FMOD directly to tumorigenic, or tumor cells to inhibit their growth. For example, one can administer to a subject in need thereof a composition comprising an effective amount of fibromodulin (FMOD) to a site having tumorigenic or tumor cells in the subject to cause the tumorigenic cells or tumor cells to stop growth or growing at a slower rate.

EGFP reporter activated in BJ-FreP colonies after 3-week FMOD treatment. (d) Western blotting revealed FMOD increased BJ cell NANOG, OCT4, and SOX2 expression during reprogramming. qRT-PCR revealed FMOD significantly induced NANOG (e), SOX2 (f), and OCT4 (g) transcription in BJ fibroblasts during reprogramming. (h) BJ-FreP colonies express similar but not identical pluripotent markers compared to iPS colonies. FMOD modulates BJ cell SMAD3 activation/phosphorylation (i) but not protein or mRNA expression (j). N=3.*, significant difference ($P<0.05$). Scale bars, 100 μm.

Figure 3:
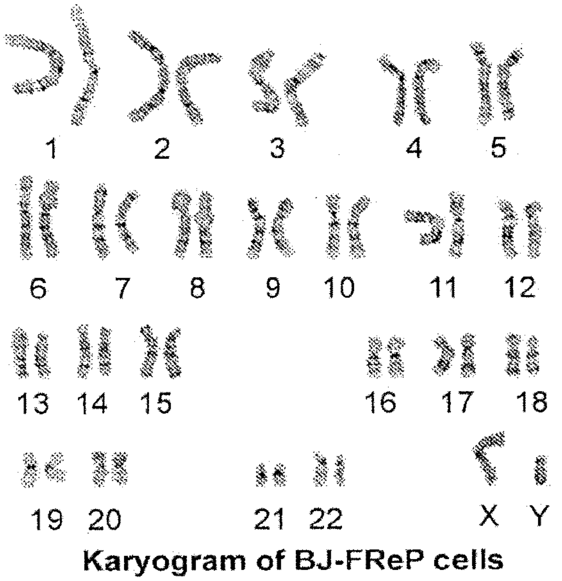

FIG. 3 summarizes test results showing no abnormities were detected in BJ-FReP cells by karyotyping.

Figure 4:
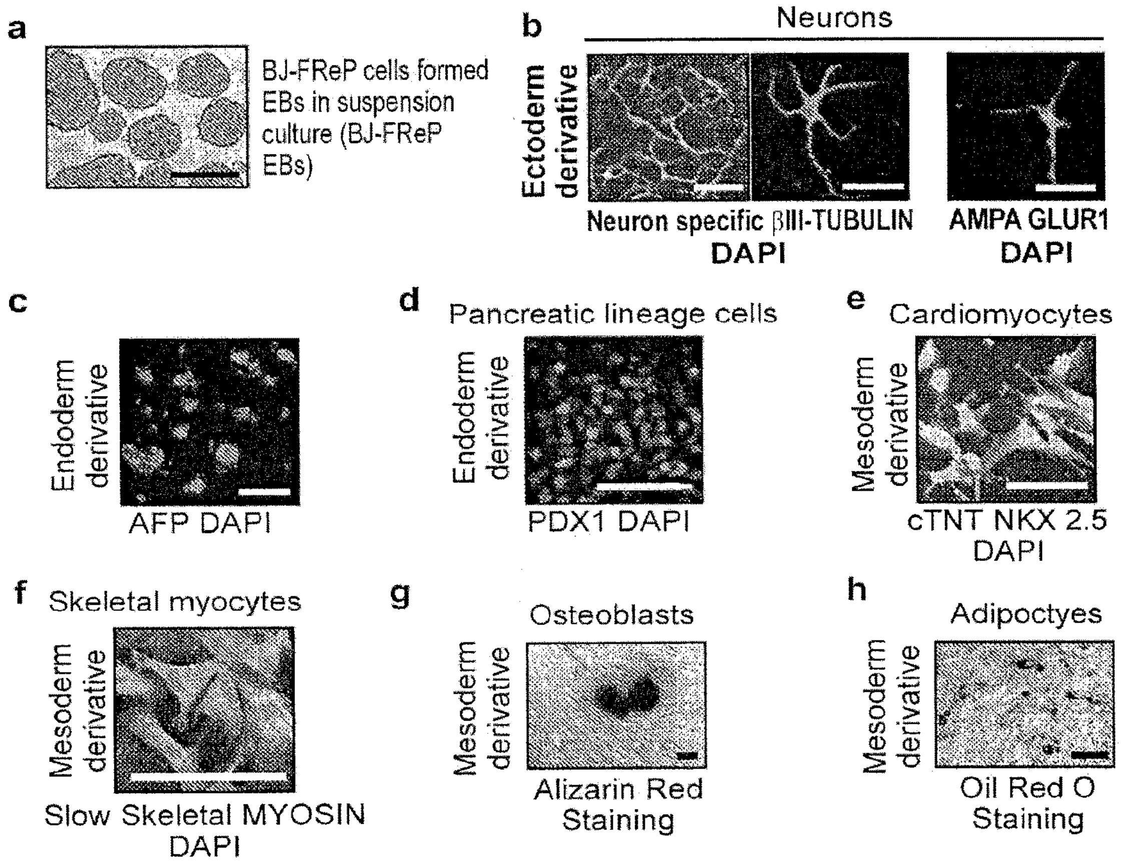

FIG. 4 summarizes test results showing that BJ-FreP cells exhibit multipotent differentiation potential in vitro. (a) BJ-FreP cells formed Ebs in suspension culture (day 2). Multipotent differentiation potential of BJ-FreP in vitro was also shown: Ectoderm—note neuron-like morphology [(b); neuron specific βIII-TUBULIN and AMPA Glutamate receptor 1 (GLUR1) expression]; Endoderm—note definitive endoderm [(c) α-fetoprotein AFP] expression in early differentiation stage] and pancreatic lineage cells [(d) pancreatic/duodenal homeobox 1 (PDX1) expression]; Mesoderm—note differentiation of cardiomyocytes [(e) cTNT and NKX2.5 co-expression], skeletal myocytes [(f); slow skeletal myosin expression], osteoblasts [(g); Alizarin Red staining], and adipocytes [(h); Oil Red 0 staining]. Scale bars, 200 μm.

FIG. 5 summarizes test results showing that BJ-FreP cells generate bone and skeletal muscles in vivo. (a) Pre-differentiated BJ-FreP cells on DBX generated new bone tissue 8 weeks post implantation in SCID mice. IHC for RUNX2 and OCN confirmed osteoblastic differentiation and anti-human MHC Class 1 MC confirmed their human origins [negative control without anti-human MHC Class 1 antibody]. (b) Pre-differentiated BJ-FreP cells were implanted in SCID mice and harvested after 8 weeks. IHC using anti-human slow skeletal myosin and two separate anti-human MHC Class 1 antibodies confirmed human skeletal muscle. (c) Cardiotoxin-injured gastrocnemius muscle of SCID mice treated with PBS resulted in severe muscle degeneration at 3 weeks. In contrast, pre-differentiated BJ-FreP cells injected into the cardiotoxin-damaged SCID mouse gastrocnemius muscle displayed minimal host/mouse muscle degeneration (black arrows) and abundant muscle regeneration by cells staining positive for human MHC Class 1 (red arrows) 3 weeks post-injection Scale bars, 200 μm.

FIG. 6 summarizes undifferentiated BJ-FreP cells did not generate tumor in vivo. Unlike control ES cells, undifferentiated BJ-FreP cells did not result in teratoma formation in SCID-beige mice kidney (6*b*) and testis (6*c*). However, H&E staining showed a small area of scattered calcified nodules in the testis, the majorly of the testis was composed of normal seminiferous tubules and uninvolved (6*c*).

Figure 7:
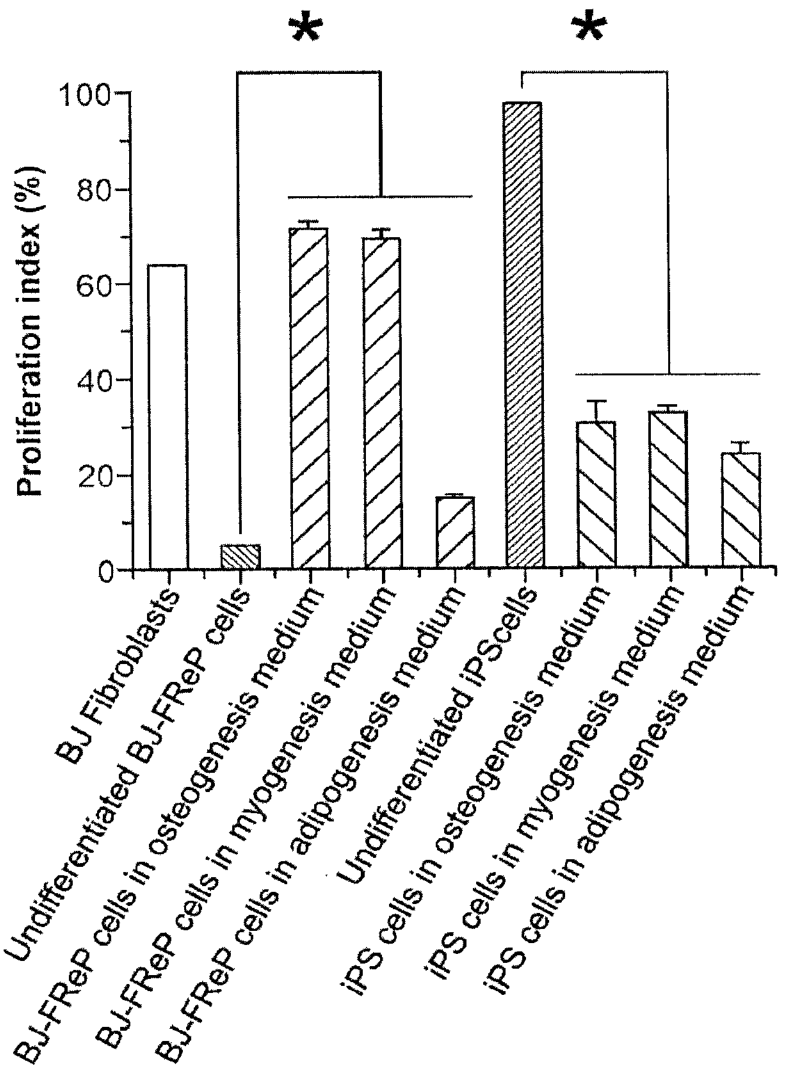

FIG. 7 summarizes undifferentiated BJ-FReP cells proliferated significantly slower than undifferentiated iPS cells. BJ-FReP cell proliferation significantly increased during differentiation. iPS cell proliferation markedly decreased during differentiation. N=3. *, significant difference ($P<0.05$).

Figure 8:
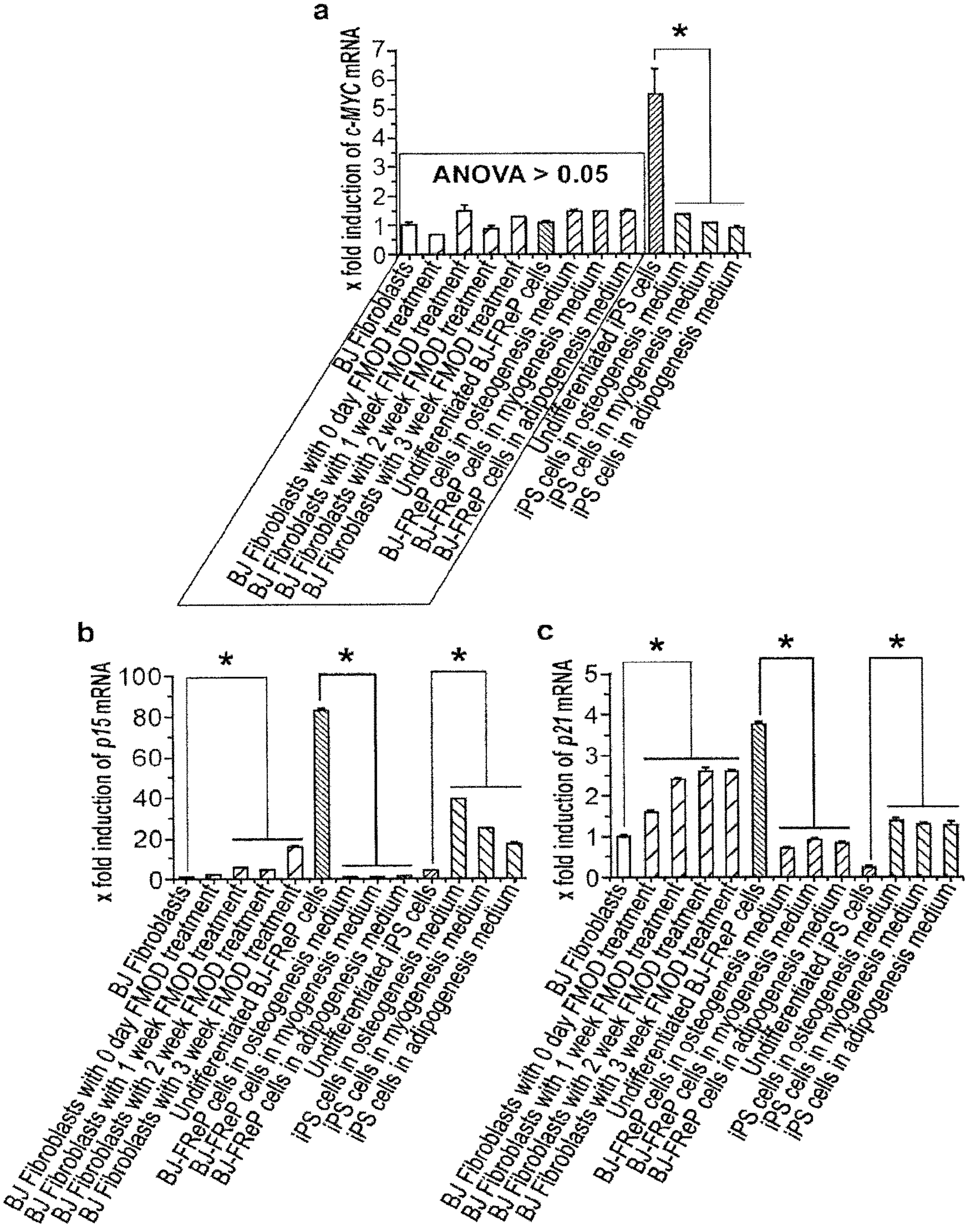

FIG. 8 summarizes that c-MYC expression was not induced during or after FMOD reprogramming of BJ cells, while iPS cells expressed high c-MYC (a). FMOD significantly increased $p15^{(Ink4B)}$ (b) and $p21^{(WAF1/Cip1)}$(c) transcription in BJ cells, respectively. N=3. *, significant difference ($P<0.05$).

Figure 9:
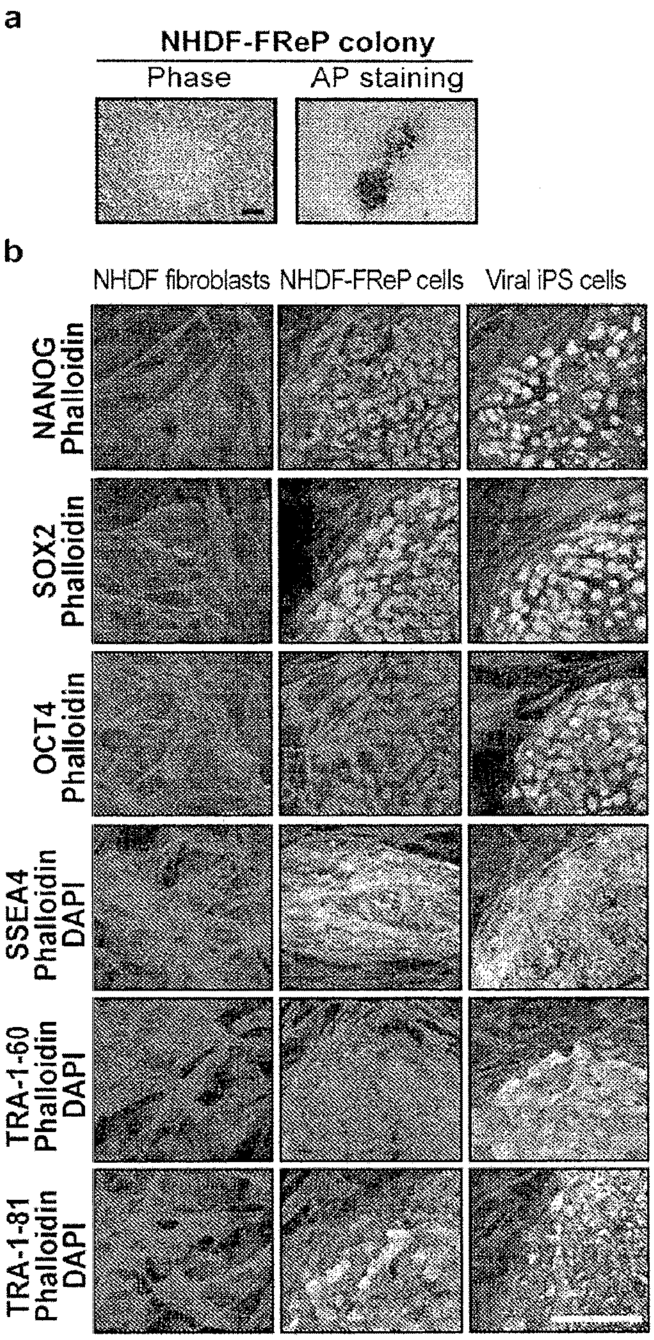

FIG. 9 summarizes test results showing FMOD protein induces ES cell-like colonies with in vitro pluripotent potential from adult normal human dermal fibroblasts (NHDF). (a) Primary adult normal human dermal fibroblasts (NHDF) formed ES cell-like and AP positive colonies after continuous exposure to FMOD protein (NHDF-FreP colony). (b) NHDF-FreP colonies express pluripotency markers NANOG, OCT4, SOX2, SSEA4, TRA-1-60 and TRA-1-81. Scale bars, 200 μm.

Figure 10:
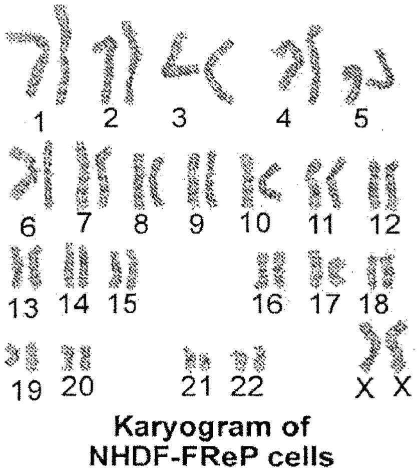

FIG. 10 summarizes test results showing that no abnormities were detected in NHDF-FReP cells by karyotyping.

Figure 11:
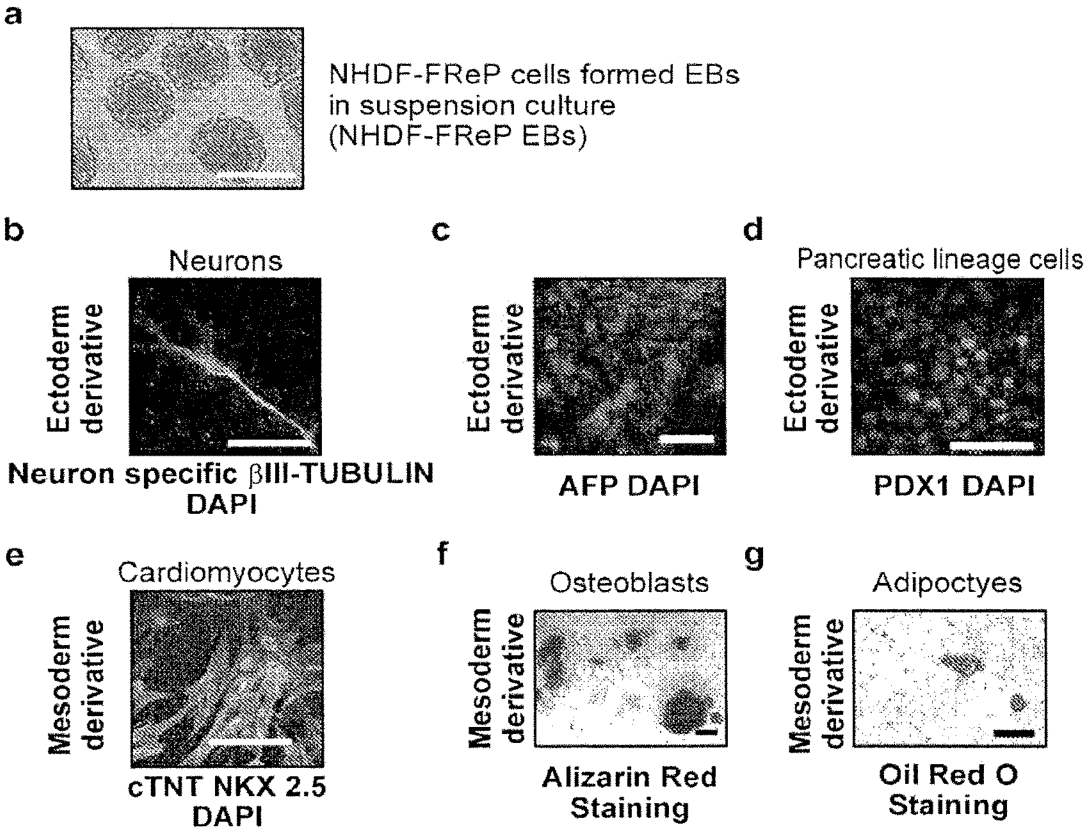

FIG. 11 summarizes test results showing NHDF-FreP cells exhibit multipotent differentiation potential in vitro. (a) NHDF-FreP cells formed embryoid bodies (Ebs) in suspension culture (day 2). Multiple differentiation potential of NHDF-FreP in vitro: Ectoderm—note neuron-like morphology [(b); neuron specific βIII1-TUBULIN]; Endoderm—note definitive endoderm [α-fetoprotein (AFP) expression in early differentiation stage (c)] and pancreatic lineage cells [(d) pancreatic/duodenal homeobox 1 (PDX1) expression]; Mesoderm—note differentiation of cardiomyocytes [(e) cardiac troponin T (cTNT) and NKX2.5 co-expression], osteoblasts [(f); Alizarin Red staining], and adipocytes [(g); Oil Red 0 staining]. Scale bars, 200 μm.

Figure 12:
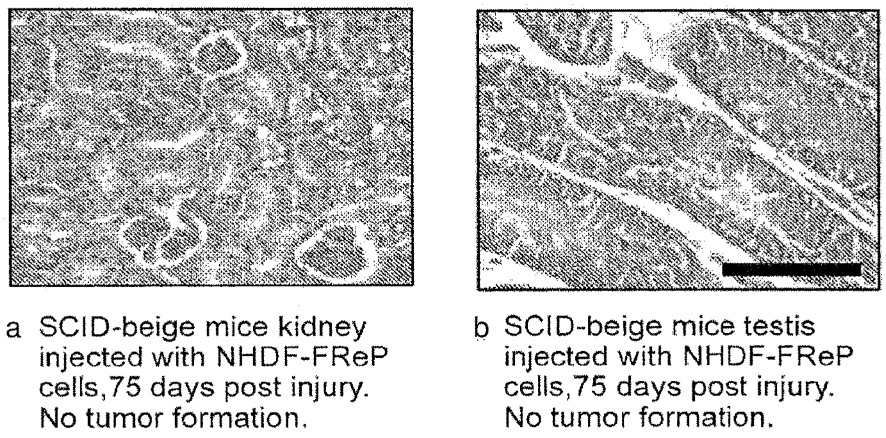

FIG. 12 summarizes test results showing that undifferentiated NHDF-FreP cells did not generate tumor in vivo.

DETAILED DESCRIPTION OF EXEMPLARY EMBODIMENTS

In one aspect of the present invention, it is provided a cell culture medium composition comprising fibromodulin (FMOD) or a derivative or fragment thereof, wherein the composition is effective for reprogramming a cell to form a FMOD reprogrammed (FReP) cell, wherein the FReP cell expresses NANOG and does not form teratoma in vivo.

In some embodiments of the cell culture medium, the FMOD has a concentration from about 200 nM to about 800 nM.

In some embodiments, the culture medium can include a FMOD protein or peptide in a concentration from about 1 nM to about 1000 μM, e.g., from about 1 nM to about 10 nM, from about 1 nM to about 20 nM, from about 1 nM to about 50 nM, from about 1 nM to about 100 nM, from about 1 nM to about 200 nM, from about 1 nM to about 500 nM, from about 1 nM to about 1000 nM, from about 1 nM to about 2 μM, from about 1 nM to about 5 μM, from about 1 nM to about 10 μM, from about 1 nM to about 20 μM, from about 1 nM to about 50 μM, from about 1 nM to about 100 μM, from about 1 nM to about 200 μM, or from about 1 nM to about 500 μM.

In some embodiments, the culture medium can include a FMOD protein or peptide in a concentration from about 10 nM to about 1000 μM, e.g., from about 10 nM to about 20 nM, from about 10 nM to about 50 nM, from about 10 nM to about 100 nM, from about 10 nM to about 200 nM, from about 10 nM to about 500 nM, from about 10 nM to about 1000 nM, from about 10 nM to about 2 μM, from about 10 nM to about 5 μM, from about 10 nM to about 10 μM, from about 10 nM to about 20 μM, from about 10 nM to about 50 μM, from about 10 nM to about 100 μM, from about 10 nM to about 200 μM, or from about 10 nM to about 500 μM.

In some embodiments, the culture medium can include a FMOD protein or peptide in a concentration from about 20 nM to about 1000 μM, e.g., from about 20 nM to about 50 nM, from about 20 nM to about 100 nM, from about 20 nM to about 200 nM, from about 20 nM to about 500 nM, from about 20 nM to about 1000 nM, from about 20 nM to about 2 μM, from about 20 nM to about 5 μM, from about 20 nM to about 10 μM, from about 20 nM to about 20 μM, from about 20 nM to about 50 μM, from about 20 nM to about 100 μM, from about 20 nM to about 200 μM, or from about 20 nM to about 500 μM.

In some embodiments, the culture medium can include a FMOD protein or peptide in a concentration from about 50 nM to about 1000 μM, e.g., from about 50 nM to about 100 nM, from about 50 nM to about 200 nM, from about 50 nM to about 500 nM, from about 50 nM to about 1000 nM, from about 50 nM to about 2 μM, from about 50 nM to about 5 μM, from about 50 nM to about 10 μM, from about 50 nM to about 20 μM, from about 50 nM to about 50 μM, from about 50 nM to about 100 μM, from about 50 nM to about 200 μM, or from about 50 nM to about 500 μM.

In some embodiments, the culture medium can include a FMOD protein or peptide in a concentration from about 100 nM to about 1000 μM, e.g., from about 100 nM to about 200 nM, from about 100 nM to about 500 nM, from about 100 nM to about 1000 nM, from about 100 nM to about 2 μM, from about 100 nM to about 5 μM, from about 100 nM to about 10 μM, from about 100 nM to about 20 μM, from about 100 nM to about 50 μM, from about 100 nM to about 100 μM, from about 100 nM to about 200 μM, or from about 100 nM to about 500 μM.

In some embodiments, the culture medium can include a FMOD protein or peptide in a concentration from about 200 nM to about 1000 μM, e.g., from about 200 nM to about 500 nM, from about 200 nM to about 1000 nM, from about 200 nM to about 2 μM, from about 200 nM to about 5 μM, from about 200 nM to about 10 μM, from about 200 nM to about 20 μM, from about 200 nM to about 50 μM, from about 200 nM to about 100 μM, from about 200 nM to about 200 μM, or from about 200 nM to about 500 μM.

In some embodiments, the culture medium can include a FMOD protein or peptide in a concentration from about 500 nM to about 1000 μM, e.g., from about 500 nM to about 1000 nM, from about 500 nM to about 2 μM, from about 500 nM to about 5 μM, from about 500 nM to about 10 μM, from about 500 nM to about 20 μM, from about 500 nM to about 50 μM, from about 500 nM to about 100 μM, from about 500 nM to about 200 μM, or from about 500 nM to about 500 μM.

In some embodiments, the culture medium can include a FMOD protein or peptide in a concentration from about 1000 nM to about 1000 μM, e.g., from about 1000 nM to about 2 μM, from about 1000 nM to about 5 μM, from about 1000 nM to about 10 μM, from about 1000 nM to about 20 μM, from about 1000 nM to about 50 μM, from about 1000 nM to about 100 μM, from about 1000 nM to about 200 μM, or from about 1000 nM to about 500 μM.

In some embodiments, the culture medium can include a FMOD protein or peptide in a concentration from about 2 μM to about 1000 μM, e.g., from about 2 μM to about 5 μM, from about 2 μM to about 10 μM, from about 2 μM to about 20 μM, from about 2 μM to about 50 μM, from about 2 μM to about 100 μM, from about 2 μM to about 200 μM, or from about 2 μM to about 500 μM.

In some embodiments, the culture medium can include a FMOD protein or peptide in a concentration from about 5 μM to about 1000 μM, e.g., from about 5 μM to about 10 μM, from about 5 μM to about 20 μM, from about 5 μM to about 50 μM, from about 5 μM to about 100 μM, from about 5 μM to about 200 μM, or from about 5 μM to about 500 μM.

In some embodiments, the culture medium can include a FMOD protein or peptide in a concentration from about 10 μM to about 1000 μM, e.g., from about 10 μM to about 20 μM, from about 10 μM to about 50 μM, from about 10 μM to about 100 μM, from about 10 μM to about 200 μM, or from about 10 μM to about 500 μM.

In some embodiments, the culture medium can include a FMOD protein or peptide in a concentration from about 20 μM to about 1000 μM, e.g., from about 20 μM to about 50 μM, from about 20 μM to about 100 μM, from about 20 μM to about 200 μM, or from about 20 μM to about 500 μM.

In some embodiments, the culture medium can include a FMOD protein or peptide in a concentration from about 50 μM to about 1000 μM, e.g., from about 50 μM to about 100 μM, from about 50 μM to about 200 μM, or from about 50 μM to about 500 μM.

In some embodiments, the culture medium can include a FMOD protein or peptide in a concentration from about 100 μM to about 1000 μM, e.g., from about 100 μM to about 200 μM, or from about 100 μM to about 500 μM.

In some embodiments, the culture medium can include a FMOD protein or peptide in a concentration from about 500 μM to about 1000 μM.

Examples of the concentration of FMOD protein or peptide in the culture medium can be, e.g., about 10 nM, about 20 nM, about 50 nM, about 100 nM, about 200 nM (e.g., 220 nM), about 500 nM, about 1000 nM, about 2 μM, about 5 μM, about 10 μM, about 20 μM, about 50 μM, about 100 μM, about 200 μM, or about 500 μM.

In some embodiments of the cell culture medium, optionally in combination with any or all of the above various embodiments, the cell is a human cell, mouse cell, and rat cell. In some embodiments, the cell can be a BJ fibroblast or primary adult normal human dermal fibroblast (HDF).

In some embodiments of the cell culture medium, optionally in combination with any or all of the above various embodiments, reprogramming is without using a genome-integrated transcription factor.

In another aspect of the present invention, it is provided a method of pluripotency reprogramming, comprising:

treating a mammalian cell with a cell culture medium comprising fibromodulin (FMOD) or a derivative or fragment thereof for a period ranging from a day to a month, and changing the cell culture medium regularly until a FMOD reprogrammed (FReP) cell forms;

wherein the FReP cell expresses NANOG and does not form teratoma in vivo.

In some embodiments of the method, optionally in combination with any or all of the above various embodiments, the FMOD has a concentration from about 200 nM to about 800 nM.

In some embodiments, the culture medium can include a FMOD protein or peptide in a concentration from about 1 nM to about 1000 μM, e.g., from about 1 nM to about 10 nM, from about 1 nM to about 20 nM, from about 1 nM to about 50 nM, from about 1 nM to about 100 nM, from about 1 nM to about 200 nM, from about 1 nM to about 500 nM, from about 1 nM to about 1000 nM, from about 1 nM to about 2 μM, from about 1 nM to about 5 μM, from about 1 nM to about 10 μM, from about 1 nM to about 20 μM, from about 1 nM to about 50 μM, from about 1 nM to about 100 μM, from about 1 nM to about 200 μM, or from about 1 nM to about 500 μM.

In some embodiments, the culture medium can include a FMOD protein or peptide in a concentration from about 10 nM to about 1000 μM, e.g., from about 10 nM to about 20 nM, from about 10 nM to about 50 nM, from about 10 nM to about 100 nM, from about 10 nM to about 200 nM, from about 10 nM to about 500 nM, from about 10 nM to about 1000 nM, from about 10 nM to about 2 μM, from about 10 nM to about 5 μM, from about 10 nM to about 10 μM, from about 10 nM to about 20 μM, from about 10 nM to about 50 μM, from about 10 nM to about 100 μM, from about 10 nM to about 200 μM, or from about 10 nM to about 500 μM.

In some embodiments, the culture medium can include a FMOD protein or peptide in a concentration from about 20 nM to about 1000 μM, e.g., from about 20 nM to about 50 nM, from about 20 nM to about 100 nM, from about 20 nM to about 200 nM, from about 20 nM to about 500 nM, from about 20 nM to about 1000 nM, from about 20 nM to about 2 μM, from about 20 nM to about 5 μM, from about 20 nM to about 10 μM, from about 20 nM to about 20 μM, from about 20 nM to about 50 μM, from about 20 nM to about 100 μM, from about 20 nM to about 200 μM, or from about 20 nM to about 500 μM.

In some embodiments, the culture medium can include a FMOD protein or peptide in a concentration from about 50 nM to about 1000 μM, e.g., from about 50 nM to about 100 nM, from about 50 nM to about 200 nM, from about 50 nM to about 500 nM, from about 50 nM to about 1000 nM, from about 50 nM to about 2 μM, from about 50 nM to about 5 μM, from about 50 nM to about 10 μM, from about 50 nM to about 20 μM, from about 50 nM to about 50 μM, from about 50 nM to about 100 μM, from about 50 nM to about 200 μM, or from about 50 nM to about 500 μM.

In some embodiments, the culture medium can include a FMOD protein or peptide in a concentration from about 100 nM to about 1000 μM, e.g., from about 100 nM to about 200 nM, from about 100 nM to about 500 nM, from about 100 nM to about 1000 nM, from about 100 nM to about 2 μM, from about 100 nM to about 5 μM, from about 100 nM to about 10 μM, from about 100 nM to about 20 μM, from about 100 nM to about 50 μM, from about 100 nM to about 100 μM, from about 100 nM to about 200 μM, or from about 100 nM to about 500 μM.

In some embodiments, the culture medium can include a FMOD protein or peptide in a concentration from about 200 nM to about 1000 μM, e.g., from about 200 nM to about 500 nM, from about 200 nM to about 1000 nM, from about 200 nM to about 2 μM, from about 200 nM to about 5 μM, from about 200 nM to about 10 μM, from about 200 nM to about 20 μM, from about 200 nM to about 50 μM, from about 200 nM to about 100 μM, from about 200 nM to about 200 μM, or from about 200 nM to about 500 μM.

In some embodiments, the culture medium can include a FMOD protein or peptide in a concentration from about 500 nM to about 1000 μM, e.g., from about 500 nM to about 1000 nM, from about 500 nM to about 2 μM, from about 500 nM to about 5 μM, from about 500 nM to about 10 μM, from about 500 nM to about 20 μM, from about 500 nM to about 50 μM, from about 500 nM to about 100 μM, from about 500 nM to about 200 μM, or from about 500 nM to about 500 μM.

In some embodiments, the culture medium can include a FMOD protein or peptide in a concentration from about 1000 nM to about 1000 μM, e.g., from about 1000 nM to about 2 μM, from about 1000 nM to about 5 μM, from about 1000 nM to about 10 μM, from about 1000 nM to about 20 μM, from about 1000 nM to about 50 μM, from about 1000 nM to about 100 μM, from about 1000 nM to about 200 μM, or from about 1000 nM to about 500 μM.

In some embodiments, the culture medium can include a FMOD protein or peptide in a concentration from about 2 μM to about 1000 μM, e.g., from about 2 μM to about 5 μM, from about 2 μM to about 10 μM, from about 2 μM to about 20 μM, from about 2 μM to about 50 μM, from about 2 μM to about 100 μM, from about 2 μM to about 200 μM, or from about 2 μM to about 500 μM.

In some embodiments, the culture medium can include a FMOD protein or peptide in a concentration from about 5 μM to about 1000 μM, e.g., from about 5 μM to about 10 μM, from about 5 μM to about 20 μM, from about 5 μM to about 50 μM, from about 5 μM to about 100 μM, from about 5 μM to about 200 μM, or from about 5 μM to about 500 μM.

In some embodiments, the culture medium can include a FMOD protein or peptide in a concentration from about 10 μM to about 1000 μM, e.g., from about 10 μM to about 20 μM, from about 10 μM to about 50 μM, from about 10 μM to about 100 μM, from about 10 μM to about 200 μM, or from about 10 μM to about 500 μM.

In some embodiments, the culture medium can include a FMOD protein or peptide in a concentration from about 20 μM to about 1000 μM, e.g., from about 20 μM to about 50 μM, from about 20 μM to about 100 μM, from about 20 μM to about 200 μM, or from about 20 μM to about 500 μM.

In some embodiments, the culture medium can include a FMOD protein or peptide in a concentration from about 50 μM to about 1000 μM, e.g., from about 50 μM to about 100 μM, from about 50 μM to about 200 μM, or from about 50 μM to about 500 M.

In some embodiments, the culture medium can include a FMOD protein or peptide in a concentration from about 100 μM to about 1000 μM, e.g., from about 100 μM to about 200 μM, or from about 100 μM to about 500 μM.

In some embodiments, the culture medium can include a FMOD protein or peptide in a concentration from about 500 μM to about 1000 μM.

Examples of the concentration of FMOD protein or peptide in the culture medium can be, e.g., about 10 nM, about 20 nM, about 50 nM, about 100 nM, about 200 nM (e.g., 220 nM), about 500 nM, about 1000 nM, about 2 μM, about 5 μM, about 10 μM, about 20 M, about 50 μM, about 100 μM, about 200 μM, or about 500 μM.

In some embodiments of the method, optionally in combination with any or all of the above various embodiments, the cell is a human cell, mouse cell, and rat cell. Examples of human cells include, e.g., BJ, MRC-5, HDF, keratinocytes, melanocytes, peripheral blood cells (e.g., CD34+), cord blood cells or even certain stem cells (e.g., adipose-derived stem cells, perivascular stem cells, neural stem cells).

In some embodiments of the method, optionally in combination with any or all of the above various embodiments, the cell is a BJ fibroblast or primary adult normal human dermal fibroblast (NHDF).

In some embodiments of the method, optionally in combination with any or all of the above various embodiments, the method is carried out without using a genome-integrated transcription factor.

In a further aspect of the present invention, it is provided a fibromodulin (FMOD) reprogrammed (FReP) cell, which FReP cell is generated by a method comprising:

treating a mammalian cell with a cell culture medium for a period ranging from a day to a month, and changing the cell culture medium regularly until the FReP cell forms;

wherein the medium comprises fibromodulin (FMOD) or a derivative or fragment thereof, and wherein the FReP cell expresses NANOG and does not form teratoma in vivo.

In some embodiments of the FReP cell, optionally in combination with any or all of the above various embodiments, the FMOD has a concentration from about 200 nM to about 800 nM.

In some embodiments of the FReP cell, optionally in combination with any or all of the above various embodiments, the cell is a human cell, mouse cell, and rat cell. Examples of human cells include, e.g., BJ, MRC-5, HDF, keratinocytes, melanocytes, peripheral blood cells (e.g., CD34+), cord blood cells or even certain stem cells (e.g., adipose-derived stem cells, perivascular stem cells, neural stem cells).

In some embodiments of the FReP cell, optionally in combination with any or all of the above various embodiments, the mammalian cell is a BJ fibroblast or primary adult normal human dermal fibroblast (NHDF).

In another aspect of the present invention, it is provided a method of treating a disorder in a mammal, which method comprising administering to the mammal a FReP cell disclosed herein above and/or below.

In some embodiments of the method, optionally in combination with any or all of the above various embodiments, the mammal is a human being.

In some embodiments of the method, optionally in combination with any or all of the above various embodiments, the disorder is a neurodegenerative disorder.

In some embodiments of the method, optionally in combination with any or all of the above various embodiments, the disorder is a central nervous system (CNS) disease, cardiovascular disease, blood diseases, Crohn's disease, bone disease, muscle disease, or chondrocyte disease.

In some embodiments of the method, optionally in combination with any or all of the above various embodiments, the disorder is a retina disease, a trauma and injury to a tissue, a skeletal disorder, an organ disease or an injury to skin, muscle, cartilage, tendon, peripheral nerve, spinal cord, blood vessels, or bone.

In a further aspect of the present invention, it is provided a supernatant, comprising a cell culture medium disclosed above or below.

In some embodiments of the supernatant, the supernatant can be included in a composition. In some embodiments, such composition can be, for example, a pharmaceutical or cosmetic composition.

In a further aspect of the present invention, it is provided a method of treating or ameliorate a disorder, comprising administering to a mammalian subject a supernatant or a composition disclosed above or below.

In further aspect of the present invention, it is provided a method or inhibiting tumor growth, comprising adding FMOD directly to tumorigenic, or tumor cells to inhibit their growth. For example, one can administer to a subject (e.g., a cancer patient) in need thereof a composition comprising an effective amount of fibromodulin (FMOD) to a site having tumorigenic or tumor cells in the subject to cause the tumorigenic cells or tumor cells to stop growth or growing at a slower rate.

As used herein, the term effective amount shall mean an amount FMOD effective to stop or slow the growth of tumor cells in the subject using a dosage regime prescribed by a medical practitioner.

As used herein, the term "grow at a slower rate" shall mean a rate of growth of the tumorigenic or tumor cells slower than their rate of growth without receiving a composition comprising FMOD described herein.

In addition to the FMOD protein or peptide or a derivative or fragment thereof, the culture medium can be any cell culture medium commonly used in the art. For example, the culture medium generally includes saline. An example of cell culture medium includes, e.g., saline, a pH of 7.4 PBS, DMEM medium, or fibroblast basic medium (FBM, Lonza). In some embodiments, the culture medium can include additional components or agents, e.g., transforming growth factor (TGF)-β.

As used herein, the term "sufficient time" shall mean a period sufficiently long to reprogram the mammalian cell by the culture medium disclosed herein. In some embodiments, the term "sufficient time" ranges from hours to about 180 days, e.g., from 8 hrs to about 12 hrs, from about 8 hrs to about 24 hrs, from about 8 hrs to about 2 days, from about 8 hrs to about 7 days, from about 8 hrs to about 14 days, from about 8 hrs to about 21 days, from about 8 hrs to about 30 days, from about 8 hrs to about 45 days, from about 8 hrs to about 60 days, from about 8 hrs to about 90 days, from about 8 hrs to about 120 days, from about 8 hrs to about 150 days, or from about 8 hrs to about 180 days.

In some embodiments, the term "sufficient time" ranges from 1 day to about 180 days, e.g., from about 1 day to about 2 days, from about 1 day to about 7 days, from about 1 day to about 14 days, from about 1 day to about 21 days, from about 1 day to about 30 days, from about 1 day to about 45 days, from about 1 day to about 60 days, from about 1 day to about 90 days, from about 1 day to about 120 days, from about 1 day to about 150 days, or from about 1 day to about 180 days.

In some embodiments, the term "sufficient time" ranges from 2 days to about 180 days, e.g., from about 2 days to about 7 days, from about 2 days to about 14 days, from about 2 days to about 21 days, from about 2 days to about 30 days, from about 2 days to about 45 days, from about 2 days to about 60 days, from about 2 days to about 90 days, from about 2 days to about 120 days, from about 2 days to about 150 days, or from about 2 days to about 180 days.

In some embodiments, the term "sufficient time" ranges from 7 days to about 180 days, e.g., from about 7 days to about 14 days, from about 7 days to about 21 days, from about 7 days to about 30 days, from about 7 days to about 45 days, from about 7 days to about 60 days, from about 7 days to about 90 days, from about 7 days to about 120 days, from about 7 days to about 150 days, or from about 7 days to about 180 days.

In some embodiments, the term "sufficient time" ranges from 14 days to about 180 days, e.g., from about 14 days to about 21 days, from about 14 days to about 30 days, from about 14 days to about 45 days, from about 14 days to about 60 days, from about 14 days to about 90 days, from about 14 days to about 120 days, from about 14 days to about 150 days, or from about 14 days to about 180 days.

In some embodiments, the term "sufficient time" ranges from 21 days to about 180 days, e.g., from about 21 days to about 30 days, from about 21 days to about 45 days, from about 21 days to about 60 days, from about 21 days to about 90 days, from about 21 days to about 120 days, from about 21 days to about 150 days, or from about 21 days to about 180 days.

In some embodiments, the term "sufficient time" ranges from 30 days to about 180 days, e.g., from about 30 days to about 45 days, from about 30 days to about 60 days, from about 30 days to about 90 days, from about 30 days to about 120 days, from about 30 days to about 150 days, or from about 30 days to about 180 days.

In some embodiments, the term "sufficient time" ranges from 45 days to about 180 days, e.g., from about 45 days to about 60 days, from about 45 days to about 90 days, from about 45 days to about 120 days, from about 45 days to about 150 days, or from about 45 days to about 180 days.

In some embodiments, the term "sufficient time" ranges from 60 days to about 180 days, e.g., from about 60 days to about 90 days, from about 60 days to about 120 days, from about 60 days to about 150 days, or from about 60 days to about 180 days.

In some embodiments, the term "sufficient time" ranges from 90 days to about 180 days, e.g., from about 90 days to about 120 days, from about 90 days to about 150 days, or from about 90 days to about 180 days.

In some embodiments, the term "sufficient time" ranges from 120 days to about 180 days, e.g., from about 12 days to about 150 days, or from about 60 days to about 180 days.

In some embodiments, the method provided herein further includes changing culture medium with fresh culture medium regularly. The term "regularly" shall mean changing culture medium hourly, bi-hourly, four times a day, twice a day, daily, once per two-day, bi-weekly, weekly, bi-monthly, or monthly.

In another aspect of the present invention, it is provided a supernatant of the FReP cell disclosed herein. The supernatant includes the culture medium of the present invention and also growth factors and/or transcriptional factors excreted by the FReP cells or clones provided herein. The supernatant disclosed herein is effective for treating or ameliorating a disorder as is the FReP cell disclosed herein. In some embodiments, the supernatant can form a composition, optionally with a carrier. The composition can be applied to a mammalian subject for treating or ameliorating a disorder. In some embodiments, the composition can be a cosmetic composition or a pharmaceutical composition.

Fibromodulin (FMOD) Reprogrammed (FReP) Cells

As used herein, the term FReP cell shall mean a cell reprogrammed by exposure to a culture medium comprising FMOD that is not a pluripotent stem cell ("PSC") but possesses at least one of the characteristics of PSC. The FReP cell disclosed herein has ability to differentiate into a desired tissue cell in a physiological condition of a tissue.

An attribute of the FReP disclosed herein is that it expresses NANOG. In some embodiments, the FReP cell disclosed herein does not form teratoma.

The characteristics or attributes of PSC are generally known in the art, some features of which are described as follows. Generally recognized characteristics of PSC include its ability to differentiate into different tissue cells under proper conditions. Other attributes of a PSC include, e.g., expression of transcriptional regulators such as OCT4, SOX2, or NANOG or antigens such as SSEA-4, TRA-1-60, or TRA-1-81, as well as high expression of alkaline phosphatase (AP).

In some embodiments, the FReP cell disclosed herein has all the attributes or a pluripotent stem cell. In these embodiments, the FReP cell is presumably a PSC.

In some embodiments, the FReP cell disclosed herein has one or more, but not all, of the attributes or a pluripotent stem cell. In these embodiments, the FReP cell disclosed herein does not amount to a PSC.

These transcriptional regulators or antigens can be readily recognized by antibodies against these regulators or antigens in, e.g., immunofluorescent staining.

As used herein, the term PSC shall also encompass pluripotent germ cells.

Generally, a FReP cell can be generated by a method comprising the steps of:

treating a mammalian cell with a cell culture medium for a period ranging from a day to a month, and changing the cell culture medium regularly until the FReP cell forms. WO 2011/143400 discloses a method of forming a pluripotent stem cell like (PSCL) cell and method of making thereof. The teaching in WO 2011/143400 is incorporated herein in its entirety.

Method of Use

The FReP cell can be used in medicine as is a PSC to treat or ameliorate a disorder in a mammal (e.g., a human being or an animal). Generally, the method includes administering to a subject having a disorder a FReP cell(s) or clone(s) so as to treat or ameliorate the disorder. Methods of using pluripotent stem cell to treat a disorder is generally established and known in the art as it will closely resemble the protocols used for embryonic stem cells (see, e.g., Sun, et al., Cell Cycle 9:5, 880-885 (2010)). Although, there are no approved products yet, there are a lot of potential applications, such as transplantation, gene repair and cell replacement therapy for a variety of genetic disorders (see, e.g., Gunaseelie, et al., *Curr Med Chem.;* 17(8): 759-766(2010)).

The disorder can be any disorder that can be treated or ameliorated by a pluripotent stem cell. In some embodiments, the disorder can be a degenerative disease such as a neurodegenerative disorder or cardiac degenerative disease.

In some embodiments, the disorder can be a central nervous system (CNS) disease, cardiovascular disease, blood diseases, Crohn's disease, bone disease, muscle disease, baldness, cancer, infertility, or chondrocyte disease, such as adenosine deaminase deficiency-related severe combined immunodeficiency (ADA-SCID), Shwachman-Bodian-Diamond syndrome (SBDS), Gaucher disease (GD) type III, Duchenne (DMD) and Becher muscular dystrophy (BMD), Parkinson disease (PD), Huntington disease (HD), juvenile-onset, type 1 diabetes mellitus (JDM), Down syndrome (DS)/trisomy 21, the carrier state of Lesch-Nyhan syndroms, Alzheimer's disease, or ischemic heart diseases (see, e.g., Gunaseelie, et al., *Curr Med Chem.;* 17(8): 759-766(2010)).

In some embodiments, the disorder can be a retina disease.

In some embodiments, the disorder can be a trauma and injury to a tissue.

Examples of such tissue can be skin, muscle, cartilage, tendon, peripheral nerve, spinal cord, blood vessels, or bone. Examples of trauma can be trauma inflicted by physical impact or trauma by a procedure in medicine, e.g., removal of tissue in treating cancer, etc.

In some embodiments, the disorder can be a skeletal disorder.

In some embodiments, the disorder can be an organ disease.

In further aspect of the present invention, it is provided a method or inhibiting tumor growth, comprising adding FMOD directly to tumorigenic, or tumor cells to inhibit their growth. For example, one can administer to a subject (e.g., a cancer patient) in need thereof a composition comprising an effective amount of fibromodulin (FMOD) to a site having tumorigenic or tumor cells in the subject to cause the tumorigenic cells or tumor cells to stop growth or growing at a slower rate, which is defined above. Administration of an effective amount of FMOD or a composition comprising an effective amount of FMOD can be achieved by systemic or local administration. Systemic administration and local administration are well understood in the art. Examples of systemic administration is parenteral injection or IV injection. Examples of local administration include e.g., injection to the local site or implantation.

EXAMPLES

The following examples illustrate, rather than limit, embodiments of the present invention.

Studies on Reprogramming Human Fibroblasts to Pluripotency Using a Single Protein, Fibromodulin Summary Pluripotent and/or multipotent stem cell-based therapeutics are a vital component of tissue engineering and regenerative medicine. The generation or isolation of safer and readily available stem cell sources will significantly aid clinical applications. We report here a technique using a single molecule, recombinant human fibromodulin protein (FMOD), to reprogram human fibroblasts into multipotent cells. Like virally-induced pluripotent stem (iPS) cells, FMOD reprogrammed (FReP) cells express pluripotency markers, form embryoid bodies (EBs), and differentiate into ectoderm, mesoderm, and endoderm derivatives in vitro. Notably, FReP cells regenerate muscle and bone tissues but do not generate teratomas in vivo. Unlike iPS cells, undifferentiated FReP cells proliferate slowly and express low proto-oncogene c-MYC and unexpectedly high levels of cyclin-dependent kinase inhibitors $p15^{Ink4B}$ and $p21^{WAF1/Cip1}$. Remarkably, in a fashion reminiscent of quiescent stem cells, the slow replicative phenotype of undifferentiated FReP cells reverses after differentiation induction, with differentiating FReP cells proliferating faster and expressing less $p15^{Ink4B}$ and $p21^{WAF1/Cip1}$ than differentiating iPS cells. Overall, single protein, FMOD-based, cell reprogramming bypasses the risks of mutation, gene instability, and malignancy associated with genetically-modified iPS cells and provides an alternative strategy for engineering patient-specific multipotent cells for basic research and therapeutic applications.

1. INTRODUCTION

Patient—specific stem cells bypass many ethical and immunologic concerns and may be created by reprogramming somatic cells into a pluripotent state. Previous studies show that a mammalian somatic cell can be reprogrammed by transferring its nucleus into an oocyte [1-3] or by fusion with an embryonic stem (ES) cell [4,5]. Recently, somatic cells were reprogrammed to gain pluripotency utilizing viral-mediated genomic integration of Yamanaka factors (Oct4, Sox2, Klf4, and c-Myc) in mouse cells, or Thomason factors (OCT4, SOX2, NANOG, and LIN28) in human cells [6,7]. These virally-induced pluripotent stem (iPS) cells resemble natural pluripotent stem cells such as ES cells in many aspects including stem cell surface markers and transcription factor expression profiles, doubling time, embryoid body (EB) formation, teratoma formation, and the capacity to differentiate into the three germ layers: endoderm, mesoderm, and ectoderm [6-10]. Despite significant promise for patient-specific cell therapy, cumbersome iPS cell reprogramming protocols as well as safety concerns over genome integrative approaches that increase iPS cell tumorigenicity have impeded clinical application [11,12]. Viral or DNA-based methodologies all exhibit varying degrees of genomic integration and insertional mutagenesis risks, making them potentially unsafe for human use [11-13].

In this study, we describe a technically straightforward method to create induced multipotent cells from somatic cells based on extracellular delivery of a single extracellular matrix (ECM) component—fibromodulin (FMOD). These FMOD reprogrammed (FReP) cells have the potential to differentiate into various therapeutic cells, but unlike iPS cells, they do not impose a risk of tumor formation from undifferentiated cells.

2. MATERIALS AND METHODS

2.1. FMOD Production cDNA of human FMOD transcript (Genebank accessory number: M 002023) was subcloned into commercially available vector pSecTag2A (Invitrogen) with C-terminal His-tag and transfected into CHO-K1 cells. After establishing a stable expression clone, FMOD was harvested from the conditioned medium and purified via ProBond™ Purification System (Invitrogen) as previously described [14].

2.2. Cell Culture

Human newborn foreskin fibroblast BJ (ATCC CRL-2522) and primary adult normal human dermal fibroblast HDF (Lonza Biosciences) cells were maintained in Clonetics® Normal Human Fibroblast Cell Systems (FGM-2; Lonza Biosciences). Viral vector-mediated human iPS (clone iPS2) [15] cells were maintained on irradiated mouse embryonic fibroblast (MEF) feeder cells (GlobalStem Inc.) in ES-DMEM/F12 (optimized for human ES cells; GlobalStem Inc.) supplemented with 20% knockout serum replacement (Invitrogen) and 10 ng/ml human recombinant fibroblast growth factor (FGF)-2 (GlobalStem Inc). Viral vector harboring enhanced green fluorescent protein gene (EGFP) derived by NANOG promoter (NANOG::EGFP reporter) was produced and infected as previously described [16].

Figure 1:
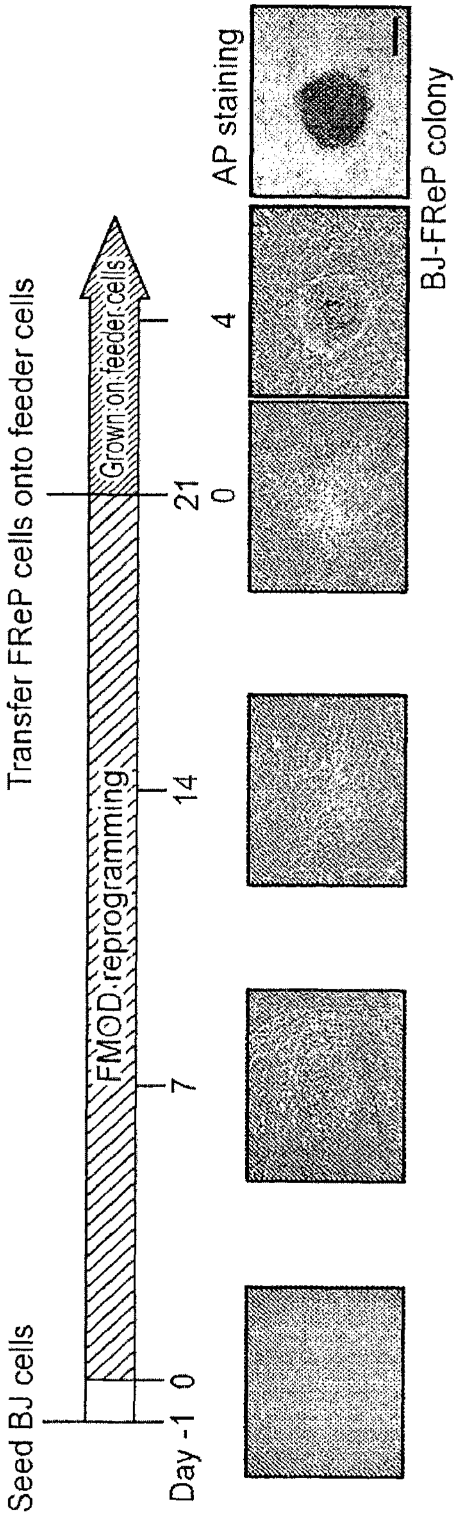
FIG. 1 shows schematic representations of the FMOD reprogramming process of invention: BJ fibroblasts were cultured in FGM-2 medium to confluence, exposed to FMOD in FBM medium without serum for 21 days, and subsequently cultured in human ES-cell media on MEF feeder cells. FMOD reprogrammed BJ cells to form ES cell-like and AP-positive (BJ-FReP) colonies on MEF feeders after 3-week exposure in serum-free condition. Scale bars, 200 μm.

2.3. FMOD Reprogramming $4\times10^5$/well human fibroblasts cultured in FGM-2 medium were seeded in 6-well cell culture plates overnight to confluence. Serum-free, growth factor-free Fibroblast Basal Medium (FBM; Lonza Biosciences) supplied with 0.4 mg/ml recombinant human FMOD, 2 mM L-glutamine (Invitrogen), and 1% penicillin/streptomycin (PS; Invitrogen) was used to treat human fibroblasts daily for three to four weeks (FIG. 1).

$1\times10^4/cm^2$ cells were seeded into 12-well culture plates for proliferation assay. After 3 days incubation, cell proliferation was analyzed by Click-iT® EdU Microplate Assay (Invitrogen).

2.4. In Vitro Differentiation

2.4.1. EBs Formation

Following manufacturer's instructions, AggreWell™ 800 Plates and AggreWell™ Medium (StemCell Technologies) were used for formation of EBs in suspension culture. Established protocols for direct differentiation of human ES and iPS cells were used for the differentiation of FReP cells with some modification [17-23].

2.4.2. Neurogenesis

For neuron differentiation, EBs were transferred into 6-well ultra-low plates with knockout DMEM medium (Invitrogen) supplied with 10% knockout serum replacement, 2 mM L-glutamine, 1% PS, 10 μM all-trans retinoic acid (RA; Sigma-Aldrich), and 100 nM of the N-terminal active fragment of human sonic hedgehog (Shh; R&D systems) to generate spheres. Fresh retinoic acid (RA) was added every day, and the medium and supplements, including Shh, were replaced every 72 h. After 8-day suspension culture, these induced spheres were transferred onto polyornithine/fibronectin (Sigma-Aldrich) coated plates with DMEM F12 medium (Invitrogen) supplied with 2% fetal bovine serum (FBS; Invitrogen), N2 supplement (Invitrogen), 20 ng/ml glial-derived neurotrophic factor (GD F; Invitrogen), 20 ng/ml brain-derived neurotrophic factor (BD F; Invitrogen), 20 ng/ml ciliary neurotrophic factor (CNTF; Invitrogen), and 1×B27 serum-free supplement (Invitrogen) [17, 18]. After 3-4 days, cultures were fixed for immunofluore scent (IF) staining.

2.4.3. Pancreagenesis

Cells were cultured in RPMI 1640 medium (Invitrogen) supplied with 2% FBS, 2 mM L-glutamine, 1% PS, and 100 ng/ml recombinant activin A (R&D systems) for 4 days for differentiation into endoderm derivative. For further induction of pancreatic lineage cells, cells with 4 days of activin A treatment were cultured for another 8 days without activin A [19,20].

2.4.4. Cardiomyogenesis

For cardiac differentiation, colonies were detached by Dispase (Invitrogen) and transferred into 6-well ultra-low plates with DMEM F12 medium supplied with 20% FBS, 1 mM nonessential amino acids (NEAA; Invitrogen), and 0.1 mM β-mercaptoethanol (Sigma-Aldrich) to initiate cardiac differentiation. During suspension culture, the medium was changed at day 1 followed by culture for another 3 days. Afterwards, the spheres were plated on AF solution (Invitrogen) coated plates for another 10 days before IF staining. Medium was changed every day [19, 21].

2.4.5. Skeletal Myogenesis

For skeletal myogenesis, colonies were transferred onto AF solution coated plates with myogenic medium I [DMEM medium supplied with 10% FBS, 10% horse serum (HS; Invitrogen), 1% chicken embryo extract (CEE; Accurate), and 1% PS] for 7 days, and then for 7-10 days in myogenic medium II [DMEM medium supplied with 1% FBS, 1% HS, 0.5%) CEE, and 1%>PS]. Half of the medium was renewed every 4 days [22].

2.4.6. Osteogenesis

For osteogenesis, colonies were transferred onto AF solution coated plates in a-MEM medium (Invitrogen) supplied with 10% FBS, 50 µg/ml ascorbic acid (Sigma-Aldrich), 10 mM β-glycerophosphate (Sigma-Aldrich), and 1% PS for 28 days. Mineralization was detected by Alizarin Red staining as previously described [23].

2.4.7. Adipogenesis hMSC Mesenchymal Stem Cell Adipogenic Differentiation Medium (Lonza Biosciences) was used for adipogenesis in vitro. Oil Red O staining was used to identify adipocytes.

2.5. Generation Offunctional Tissues In Vivo 8-week old SCID mice were anaesthetized by isoflurane/02 inhalation. For osteogenesis in vivo, a demineralized bone matrix (DBX; Musculoskeletal Transplant Foundation) was used as scaffold [23]. After 3-day pre-induction in a-MEM medium supplied with 10% FBS, 50 µg/ml ascorbic acid, 10 mM β-glycerophosphate, and 1% PS, $5\times10^5$ cells were harvested and suspended in 150 µî PBS and mixed with DBX before implantation into a pocket in the gluteofemoral muscle of SCID mice. Mice were sacrificed 8 weeks post procedure, and tissues were harvested and fixed in 10% formalin [23].

For myogenesis in vivo, $5\times10^5$ cells were cultured in myogenic medium I for 3 days, and slowly injected into a pocket of gluteofemoral muscle of SCID mice; specimen were harvested at 8 weeks post injection. Alternatively, cardiotoxin (15 µg; Sigma) was injected into the gastrocnemius muscle 3 hours prior to transplantation of $5\times10^5$ FReP cells. Mice were re-anaesthetized, and cells suspended in 35 µl PBS, or the same volume of PBS as a control, were then slowly injected into the injured muscle. Mice were sacrificed 3 weeks post-procedure and muscle tissue was harvested and fixed in 10% formalin [22].

2.6. Karyotyping and Tumor Formation

Karyotyping and tumor formation assays were performed by Applied StemCell Inc. Briefly, cells were collected by collagenase IV treatment and injected into male SCID-beige mice kidney and testis. Tissues were harvested after 3-4 months and processed for paraffin embedding and hematoxylin and eosin (H&E) staining following standard procedures.

2.7. Western Blotting

Cells were harvested with RIPA buffer (Pierce) supplemented with Halt™ Protease and Phosphatase Inhibitor Cocktail (Pierce). 15 µg of protein from each sample was loaded onto SDS-PAGE and transferred to nitrocellulose membranes as previously described [24]. Western blotting was performed using the following primary antibodies: glyceraldehyde-3-phosphate dehydrogenase (GAPDH; Santa Cruz Biotechnology, Inc.), NANOG (Cell Signaling Technology), OCT4A (Cell Signaling Technology), SMAD3 (Abeam Inc.), phosphorylated SMAD3 (pSMAD3, Abeam Inc.), and SOX2 (Cell Signaling Technology). Immu-Star™ WesternC™ kit (Biorad) was used for development. Bands on Western blot were quantified using QuantityOne® (Biorad), and values were expressed in relative arbitrary densitometry units.

2.8. RT-PCR, Quantitative RT-PCR (qRT-PCR) and PCR Array

RNAs were extracted using RNeasy® Mini Kit (Qiagen) with DNase (Qiagen) followed by reverse transcription with Superscript™ III First-Strand Synthesis System for RT-PCR (Invitrogen). PCR was performed with Taq DNA polymerase (Invitrogen). Primers used in this study are listed in Table 1 [25]. qRT-PCR was performed on a 7300 Real-Time PCR system (Applied Biosystems Inc.) with TaqMan® Gene Expression Assays (Applied Biosystems Inc.). Concomitant GAPDH was also performed in separate tubes for each RT reaction. For each gene, at least three separate sets of qRT-PCR analyses were performed from different cDNA templates. The $\Delta C_T$ levels of GAPDH did not differ significantly between treatment conditions; thus, they were used as housekeeping standard (data not shown). qBiomarker™ Screening PCR Arrays for iPSC Colony Screening (SABiosciences Corp.) were used for RNA expression profile as well.

TABLE 1

Primers used for RT-PCR [1]

| Gene | Forward primer | Reverse primer |
|---|---|---|
| NANOG | cggcttcctcctcttcctctatac (SEQ ID NO.: 1) | atcgatttcactcatcttcacacgtc (SEQ ID NO.: 2) |
| OCT3/4 | ctgcagtgtgggtttcgggca (SEQ ID NO.: 3) | cttgctgcagaagtgggtggagga (SEQ ID NO.: 4) |

TABLE 1-continued

| Primers used for RT-PCR [1] | | |
|---|---|---|
| Gene | Forward primer | Reverse primer |
| SOX2 | gagagaaagaaagggagagaag (SEQ ID NO.: 5) | gagagaggcaaactggaatc (SEQ ID NO.: 6) |
| KRT-18 | tctgtggagaacgacatcca (SEQ ID NO.: 7) | ctgtacgtctcagctctgtga (SEQ ID NO.: 8) |
| NESTIN | cagctggcgcacctcaagatg (SEQ ID NO.: 9) | agggaagttgggctcaggactgg (SEQ ID NO.: 10) |
| FLT-1 | atcagagatcaggaagcacc (SEQ ID NO.: 11) | ggaacttcatctgggtccat (SEQ ID NO.: 12) |
| VE-CADHERIN | acgggatgaccaagtacagc (SEQ ID NO.: 13) | acacactttgggctggtagg (SEQ ID NO.: 14) |
| GATA-4 | ctccttcaggcagtgagagc (SEQ ID NO.: 15) | gagatgcagtgtgctcgtgc (SEQ ID NO.: 16) |
| β-ACTIN | atctggcaccacaccttctacaatgagctgcg (SEQ ID NO.: 17) | cgtcatactcctgcttgctgatccacatctgc (SEQ ID NO.: 18) |

[1] Villa-Diza LG, Nandivada H, Ding J, Nogueira-de-Souza NC, Krebsbach PH, O'Shea KS, et al. Synthetic polymer coatings for long-term growth of human embryonic stem cells. Nat Biotechnol. 2010; 28: 581-3.

2.9. Alkaline Phosphatase (AP) Staining

AP staining was performed with the Vector Red substrate kit from Vector Laboratories.

2.10. IF and Immunohistochemistry (IHC) Staining

Samples for IF were fixed in pre-chilled acetone, and 4',6-diamidino-2-phenylindole (DAP I) was used for count staining. Meanwhile, samples for IHC were fixed in 10% formalin. After fixation, samples for IHC were dehydrated, paraffin-embedded, and sectioned at 5 μm for H&E, Masson's Trichrome, and IHC staining. IF and IHC staining were performed using the following primary antibodies: cardiac troponin t (cTNT; Abeam Inc.), α1-fetoprotein (AFP; Abeam Inc.), FLT-1 (Abeam Inc.), AMPA glutamate receptor 1 (GLUR1; Abeam Inc.), KRT-18 (Abeam Inc.), human major histocompatibility complex (MHC) Class 1 (clone H-300, Santa Cruz Biotechnology Inc.; clone EP1395Y, Abeam Inc.), MYOSIN (Skeletal, slow) (Sigma-Aldrich), osteocalcin (OCN, Santa Cruz Biotechnology), NANOG (Cell Signaling Technology), NESTIN (Abeam Inc.), NKX2.5 (Abeam Inc.), OCT4A (Cell Signaling Technology), pancrease/duodenum homoeobox 1 (PDX1; Abeam Inc.), runt-related transcription factor 2 (RUNX2, Santa Cruz Biotechnology, Inc.), SOX2 (Cell Signaling Technology), SSEA4 (Cell Signaling Technology), TRA-1-60 (Cell Signaling Technology), TRA-1-81 (Cell Signaling Technology), neuron specific βIII-TUBULIN (Abeam Inc.), VE-CADHERIN (Abeam Inc.), and Alexa Fluor® 594-Phalloidin (Invitrogen).

2.11. Statistical Analysis

Results were graphically depicted as the mean±standard error of mean (s.e.m). Statistical significance was computed using ANOVA and Tukey-Fisher LSC criterion based on the post hoc t statistics. Independent-samples t-test was used to analyze experiments of two groups. All statistical analyses in this manuscript were as per consultation with the UCLA Statistical Biomathematical Consulting Clinic (SBCC).

3. RESULTS 3.1. FMOD Reprograms Human Fibroblasts

Figure 2:
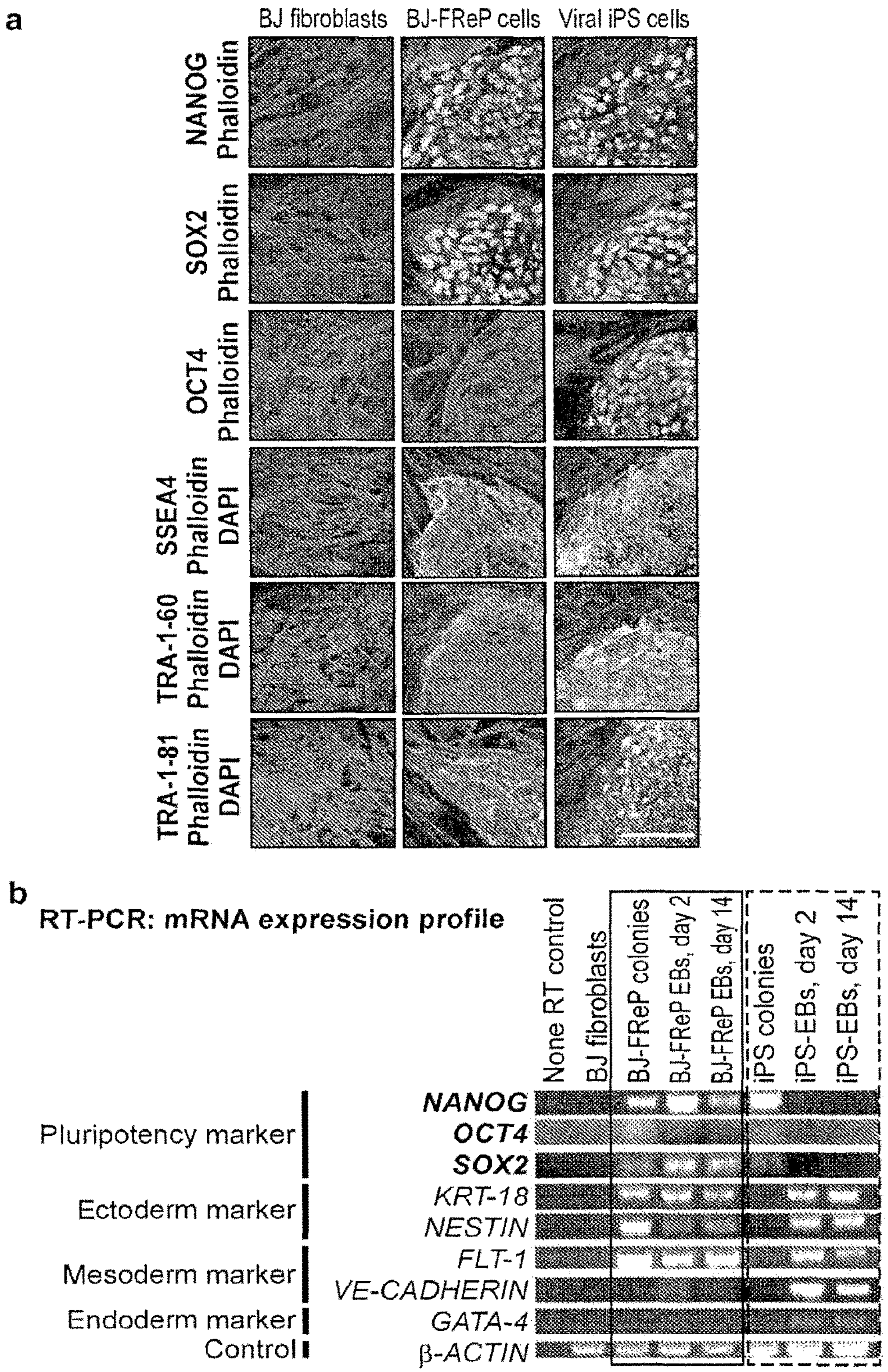
FIG. 2 summarizes test results showing that FreP cells exhibit pluripotent markers. (a) IF staining demonstrated that BJ-FreP colonies expressed pluripotency markers. (b) RT-PCR profile of markers for pluripotency (NANOG, OCT4, SOX2), ectoderm (KRT-18, NESTIN), mesoderm (FLT-1, VE-CADHERIN), and endoderm (GATA-4) are similar but not identical between BJ-FreP and iPS cells and their respective Ebs. Control (β-ACTIN). (c) NANOG.
Figure 2:
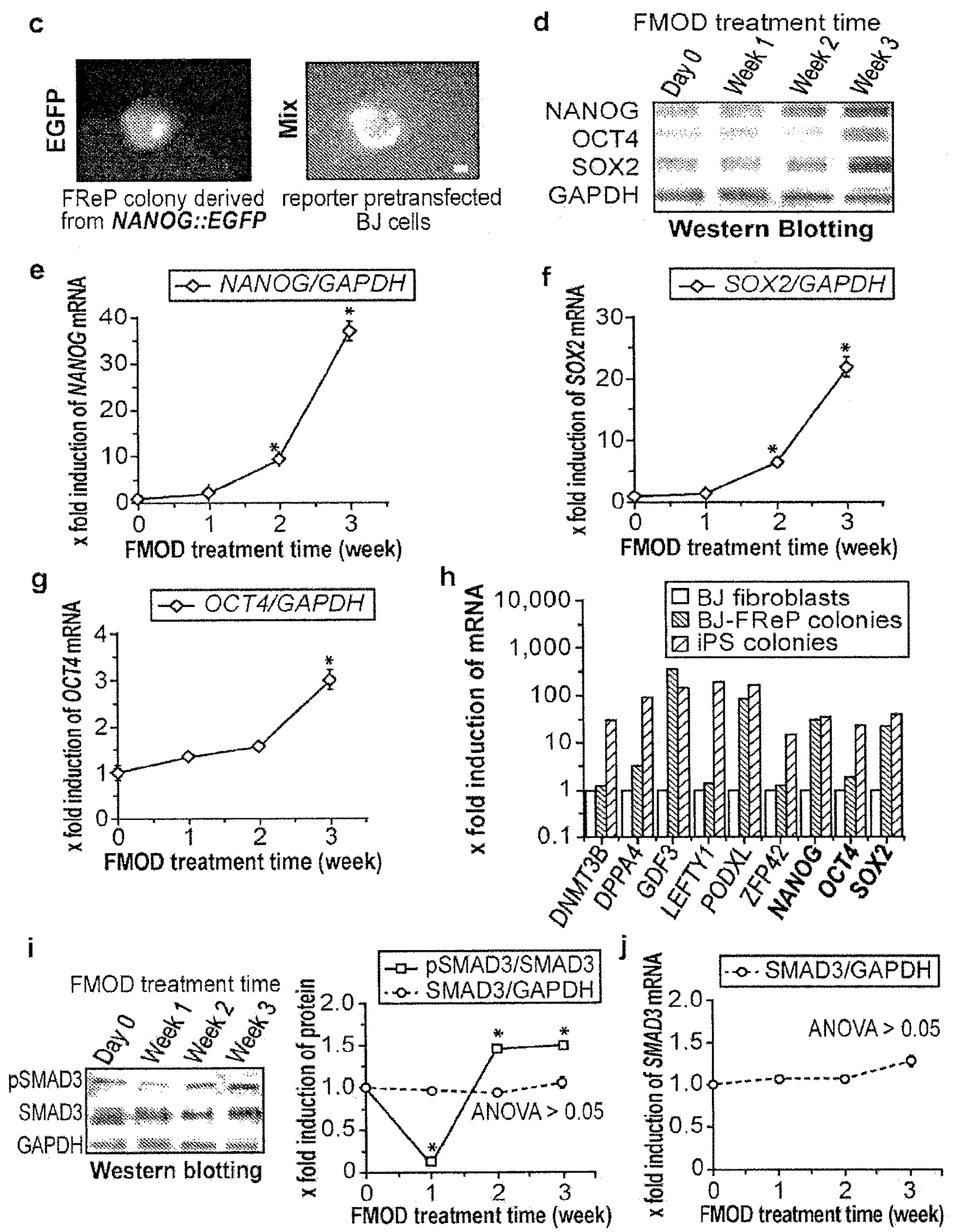

Human newborn foreskin fibroblast BJ cells exposed to continuous recombinant human FMOD under serum-free conditions formed AP-positive, ES cell-like colonies on MEF feeders at an average frequency of 0.03% (32±2.6 ES cell-like colonies from 100,000 BJ fibroblasts, N=16) (FIG. 1). The 0.03% FMOD-mediated reprogramming efficiency is comparable to original retroviral-mediated iPS cell reprogramming rates [6, 7]. FMOD-induced ES cell-like colonies expressed several ES/iPS cell pluripotency markers, including core transcriptional regulators of pluripotent cells (NANOG, SOX2, and OCT4), and common pluripotent cell surface antigen (SSEA4, TRA-1-60, and TRA-1-81) (FIGS. 2*a* and *b*). Besides BJ human fibroblasts, adult normal human dermal fibroblast (NHDF) cells similarly exposed to FMOD also formed ES cell-like colonies on MEF feeders with positive AP activity and pluripotency marker expression (FIG. 9). To confirm induction of NANOG expression, a NANOG::EGFP reporter was introduced into BJ fibroblasts. As expected, NANOG::EGFP reporter was highly activated in FMOD-reprogrammed BJ (BJ-FReP) colonies (FIG. 2*c*). In addition, Western blotting and qRT-PCR revealed that besides NANOG, which is essential for embryonic and induced pluripotency [26, 27], SOX2 was also significantly upregulated starting at 2 weeks after FMOD treatment (FIGS. 2*d-f*). By week 3, NANOG, SOX2, and OCT4 were all markedly upregulated in fully-reprogrammed BJ-FReP cells (FIGS. 2*d-h*). Meanwhile, continuous FMOD exposure substantially increased phosphorylated SMAD3 (pSMAD3) levels at weeks 2 and 3 (FIGS. 2*i* and *j*). Interestingly, persistent transforming growth factor (TGF)-β/ACTIVIN/NODAL-responsive SMAD3 phosphorylation is also associated with maintenance of human ES cells in an undifferentiated state [28-33]. Additionally, karyotyping was normal in all tested FReP cells (FIG. 3 and FIG. 10). Therefore, FMOD reprogrammed (FReP) human fibroblasts resembled ES cells with respect to colony morphology, pluripotency marker expression, and sustained pSMAD3 signaling.

3.2. FReP Cells Exhibit Multipotent Differentiation Potential 3.2.1. FReP Cells Differentiate into Multiple Lineage Derivatives In Vitro Similar to human ES and iPS cells, BJ-FReP cells formed EBs (FIG. 4*a*) and strongly expressed ectoderm and mesoderm markers, but differed in the expression time course of key reprogramming genes (FIG. 2*b*). Notably, BJ-FReP-EBs, but not iPS-EBs, expressed NANOG and SOX2 at day 2 and 14 (FIG. 2*b*).

To confirm the multipotency of established FReP cells, we assessed their ability to differentiate into ectoderm, endoderm or mesoderm derivatives following protocols established for human ES and iPS cells [17-19, 21-23]. In the presence of differentiation media for neurons (ectoderm derivatives), the BJ-FReP-EBs dissociated and expanded, and most of the cells (~90%) ultimately differentiated into neurons characterized by typical neuronal morphology and expression of neuron specific βIII-TUBULIN (a broadly used ectodermal differentiation marker) and GLUR1 (an excitatory neurotransmitter receptor in the mammalian brain, and activated in a variety of normal neurophysiologic processes) (FIG. 4*b*). In differentiation medium with activin A, BJ-FReP cells stained positive for an early endodermal lineage marker AFP by day 4 (FIG. 4*c*). With another 8 days of further differentiation without activin A, these AFP-positive BJ-FReP cells further differentiated into pancreatic lineage cells, characterized by staining of PDX1, a transcription factor necessary for pancreatic development and β-cell maturation (FIG. 4*d*). Similarly, following differentiation protocols described above, we also differentiated BJ-FReP cells into several mesoderm derivatives, including cardiomyocytes [FIG. 4*e*; characterized by double staining of cTNT (a cardiomyocyte differentiation marker) and NKX2.5 (the earliest transcription factor expressed in cardiac lineage cells)], skeletal myocytes (FIG. 4*f*; characterized by staining of myosin), osteoblasts (FIG. 4*g*), and adipocytes (FIG. 4*h*). Besides BJ-FReP cells, FMOD reprogrammed NHDF (NHDF-FReP) cells also demonstrated analogous multipotency in vitro (FIG. 11). Overall, FReP cell responses to ectoderm, endoderm, and mesoderm differentiation signals appeared similar to ES/iPS cells in vitro.

3.2.2. FReP Cells Generate Bone and Skeletal Muscles In Vivo

To study their in vivo osteogenic potential, BJ-FReP cells were pre-differentiated in osteogenic medium for 3 days, loaded onto DBX scaffolds, and then implanted into the gluteofemoral muscle pocket of immunodeficient SCID mice (FIG. 5*a*). At 8 weeks post-implantation, regeneration by BJ-FReP cells was tracked by IHC with antibodies against human major MHC Class I (FIG. 5*a*). To further confirm the relative contribution of engrafted BJ-FReP cells to osteoblastogenesis, we immunostained for RUNX2— the master transcription factor specifying osteoblastic lineage commitment [34] and OCN— a mature osteoblast differentiation marker [35]. The spatial co-localization of human MHC Class I with either RUNX2 or OCN immunostaining (FIG. 5*a*) confirmed the engraftment, persistence, and differentiation of BJ-FReP cells into new bone tissue.

In a separate study, to assess in vivo myogenic potential, BJ-FReP cells underwent 3-day myogenic pre-differentiation in vitro before injection into the gluteofemoral muscle pocket of SCID mice. At 8 weeks post-injection, robust co-localization of human MHC Class I and human slow skeletal myosin confirmed BJ-FReP cell differentiation into skeletal muscle in vivo (FIG. 5*b*). To more rigorously assess muscle regeneration, we injured the recipient muscle with cardiotoxin [22, 36]. Identically pre-differentiated BJ-FReP cells were transplanted into SCID mice gastrocnemius muscle 3 hours after injury by intramuscular cardiotoxin injection. At 3 weeks post-transplant, BJ-FReP cell treated animals revealed significantly less scar tissue and muscle degeneration (FIG. 5*c*). IHC confirmed human MHC Class I-expressing myofibers, indicating also the engraftment, persistence and functional differentiation of BJ-FReP cells, this time into skeletal muscle tissue (FIG. 5*c*). Taken together, these data conclusively demonstrated the ready feasibility and ease of using FReP cells to regenerate different functional tissues in vivo using simple FMOD-based reprogramming and relatively brief (3-day) in vitro pre-differentiation protocols.

These data demonstrate the in vivo multipotency of FReP cells and highlight their potential usefulness for cell-based tissue engineering.

3.3. FReP Cells are Distinct from Classic iPS Cells 3.3.1. Teratoma Assay

To test FReP cell pluripotency and safety in vivo, we used a standard, SCID-beige mouse teratoma model injecting BJ-FReP cells or positive control human H9 ES cells into the kidney or testis. Instead of forming tumors, injected undifferentiated BJ-FReP cells developed into small, calcified nodules after 3 months (FIG. 6). NHDF-FReP cells also did not form teratoma in a separate study (Supplementary FIG. 4).

3.3.2. Proliferation Assay

Cell proliferation ratios of untreated BJ fibroblasts, undifferentiated vs. differentiating BJ-FReP cells, and undifferentiated vs. differentiating iPS cells were compared. Our studies showed that undifferentiated BJ-FReP cells proliferated minimally, while differentiating BJ-FReP cells proliferated rapidly (FIG. 7). In contrast, consistent with the requirement for increased cell cycle rates during iPS cell reprogramming [26,37], undifferentiated iPS cells proliferated significantly more rapidly than differentiating iPS cells or undifferentiated BJ-FReP cells (FIG. 7). Overall, the absence of FReP-associated teratoma and low rates of undifferentiated FReP proliferation suggest fundamental biologic differences between FReP and iPS cells.

3.3.3. Gene Expression Profile Assay

FReP and iPS cells also showed different gene expression signatures (FIG. 2*h* and FIG. 8). In particular, when compared to iPS cells, undifferentiated FReP cells exhibited relatively lower OCT4 (FIGS. 2*a* and 2*h*) and expressed ectoderm and mesoderm markers (e.g. KRT-18, NESTIN, and FLT-1) not detected in iPS cells (FIG. 2*b*). In addition, non-fully reprogrammed "pre-FReP" cells expressed NANOG (FIGS. 2*d* and *e*), while fully reprogrammed FReP cells retained NANOG, SOX2, and OCT4 expression during EB formation (FIG. 2*b*). In contrast, pre-iPS cells do not express NANOG [26]; and lose NANOG, SOX2, and OCT4 expression during iPS cell EB formation (FIG. 2*b*). Remarkably, expression of the proto-oncogene c-MYC, which critically regulates cell proliferation and transformation [38] and can induce teratoma formation [8, 39], was considerably lower in BJ-FReP than undifferentiated iPS cells by 0.18-fold (FIG. 8*a*). In contrast, cyclin-dependent kinase inhibitors, $p15^{Ink4B}$ and $p21^{WAF1/Cip1}$ which mediate TGF-β induced cell cycle arrest [40], were significantly upregulated (83.1- and 3.8-fold, respectively) in BJ-FReP but not in iPS cells (FIGS. 8*b* and *c*).

Collectively, FReP and iPS cells have distinctly different proliferative, tumorigenic, and molecular phenotypes (Table 2).

TABLE 2

Comparison of human ES, iPS, and FReP cells

| | Related FIG. | ES cells | iPS cells | FReP cells |
|---|---|---|---|---|
| ES-like colonies | | | | |
| ES-like colony formation on MEF feeder cells | FIG. 1 and FIG. 9a | Yes | Yes | Yes |
| AP activity | FIG. 1 and FIG. 9a | Yes | Yes | Yes/ Partial |
| Expression of pluripotency markers | FIG. 2a, b, and FIG. 9b | Yes | Yes | Yes |
| Expression of ectoderm markers | FIG. 2b | No | No | Yes |
| Expression of mesoderm markers | FIG. 2b | No | No | Yes |
| EBs | | | | |
| EB formation in suspension culture | FIG. 4a and FIG. 1 la | Yes | Yes | Yes |
| Expression of pluripotency markers | FIG. 2b | No | No | Yes |
| Expression of ectoderm markers | FIG. 2b | Yes | Yes | Yes |
| Expression of mesoderm markers | FIG. 2b | Yes | Yes | Yes |
| Expression of endoderm markers | FIG. 2b | Yes | Yes | Weak |
| In vitro differentiation | | | | |
| Ectoderm derivatives | FIG. 4b and FIG. 1 lb | Yes | Yes | Yes |

4. DISCUSSION

Tumorigenesis remains a significant obstacle to safe clinical application of pluripotent stem cells, such as iPS and ES cells [13, 41]. At the genetic level, one crucial difference between iPS cells and ES cells is the introduction and integration of genes, which is essential for the reprogramming process, into the genome of somatic cells. As such, iPS cells are likely to carry a higher tumorigenicity risk than ES cells due to gene activation or interruption from viral integration during reprogramming [12, 13, 42-44]. Additionally, undesirable transgene reactivation is another problem of using viral iPS cells. For example, c-Myc reactivation has shown to significantly increase tumor formation in chimeric mice generated from iPS cells [8]. While c-MYC is dispensable for iPS cells generation, reactivation of the other reprogramming factors may also cause tumors [8, 12, 13, 19, 39, 44]. Meanwhile, apart from the extremely low efficiency [12, 44-46], using adenoviruses, plasmids and chemicals to generate iPS cells does not exclude the risk of teratoma formation since genetic alterations from integration of small virus/plasmid DNA fragments or chemically induced mutations can still occur [12, 44]. Moreover, non-integrative RNA- and protein-based iPS-generation approaches are complicated by the need for cell-penetrating, cytosolic delivery [11]. Although the minimal criteria for demonstrating successful human pluripotent stem cell reprogramming is teratoma formation, teratoma formation in and of itself does not guarantee pluripotency as there are instances of mouse ES-like cells that form teratomas but do not produce germline chimeras [44]. Concurrently, significant issues impede Food and Drug Administration (FDA) approval of iPS cells for human use, including (i) undesirable use of oncogenes for reprogramming, (ii) undesirable use of retroviral or genome integrative approaches, and (iii) undesirable teratoma formation. Thus, reprogramming approaches that specifically concentrate on FDA safety issues are required [12, 47-49].

To begin addressing FDA concerns, several groups have successfully reprogrammed fibroblasts into neurons and pancreatic exocrine cells into insulin-producing beta cells without an intermediate, potentially tumorigenic, pluripotent stage [50,51]. This reflects a recent focus on safer cellular reprogramming methodologies that generate curative cell types without teratoma formation [12,44,48]. In this respect, FReP cells may fulfill both goals of functional tissue generation and teratoma prevention.

In this example, we disclose an approach that uses a single extracellular matrix (ECM) proteoglycan—FMOD, instead of genetic modifications [6,7,11,45,46], undefined embryonic stem cell extracts [4,52], or animal oocyte extracts [53,54] to generate multipotent cells useful for replacing, restoring, and/or regenerating tissue where disease or injury has caused irreparable damage to native tissues. After simple exposure to FMOD, human skin fibroblasts become at least partially reprogrammed as demonstrated by alterations in gene expression profiles (FIGS. 2*a*, 2*b*, 2*h*, and FIG. 9*b*). Notably, a set of genes characteristic of undifferentiated ES cells, NANOG, SOX2, and OCT4 [12, 44,55-59] is activated during the FMOD reprogramming (FIG. 2*d*-*g*). NANOG, SOX2, and OCT4 regulate the ES potency network by acting on promoters of thousands of ES genes and serve as the major transcription factors that collectively define ES cell identity [12,57,59-61].

We have demonstrated that the FReP cells are able to be differentiated into multiple functional cell types, including neurons, pancreatic lineage cells, cardiomyocytes, skeletal myocytes, osteoblasts, and adipocytes in vitro (FIG. 4*b*-*h* and FIG. 11*b*-*g*), suggesting a potential for multiple lineage differentiation and functional tissue regeneration. Thus far, FReP cells have generated functional tissues such as bone and skeletal muscle in vivo (FIG. 5), confirming that the observed in vitro multipotency is at least partially translated in vivo. Overall reprogramming by FMOD on upregulating NANOG, SOX2, OC4 gene associated on ES pluripotency may mimic a functional transcriptional network towards cell multipotency [62-65].

The fact that extracellular approaches can reprogram cells lends further support to our ability to reprogram fibroblasts using a single extracellular protein, FMOD [54]. The success of generating multipotent FReP cells using an extracellular protein approach has led us to explore the possible mechanism underlying FMOD-based reprogramming. Theoretically, only small molecules can freely penetrate into the cell for reprogramming. As a 59 kD ECM proteoglycan, passive entry of FMOD is unlikely. Alternatively, FMOD has been found to be a critical component for maintenance of endogenous stem cell niches [66]. Specific cellular niches or microenvironments are able to significantly modify epigenetic expression and lead to the altered cell fate [67, 68], while FMOD is known to modulate expression, organization, and function of various growth factors, cytokines, and ECM components [14, 69-75]. It is thus possible that FMOD significantly affects ECM microenvironment to promote signal pathways involved in cell reprogramming.

For instance, FMOD induces a specific, biphasic TGF-β/ACTIVIN/NODAL signaling response characterized by significantly reduced pSMAD3 levels at week 1 followed by markedly increased pSMAD3 at weeks 2 and 3 (FIG. 2*i*). Previous studies has shown that FMOD presence or absence profoundly alters TGF-β bioactivity in a fetal scarless wound repair model [14], and that TGF-β-stimulated SMAD signaling can directly upregulate NANOG expression [29]. While direct SMAD transactivation of OCT4 or SOX2 has not been described, NANOG itself can induce OCT4 or SOX2 expression [60,76]. Thus, FMOD modulation of SMAD signaling may explain the unique molecular phenotype of FReP cells wherein by week 2 of reprogramming, pluripotency genes NANOG, OCT4, and SOX2 are concurrently upregulated (FIGS. 2*d*-*g*). Theunissen et al. have demonstrated that constitutive Nanog expression, although not sufficient for pluripotency induction, does promote transition of both MEF-derived pre-iPS and neural stem (NS) cells to pluripotency under serum-free conditions with leukemia inhibitory factor (LIF); this result suggests that Nanog is able to overcome reprogramming barriers and induce pluripotency in minimal conditions [77]. Hence, increased NANOG expression through stimulation of TGF-β/ACTIVIN/ODAL-responsive SMAD signaling is likely a significant permissive pathway for FMOD-based reprogramming. In addition, early combined chemical inhibition of TGF-β and MEK signaling between weeks 1 and 2 improves human cell reprogramming efficiency [78]. Thus, it is also possible that the initial FMOD-mediated pSMAD3 reduction facilitates early reprogramming.

Unlike undifferentiated iPS cells, undifferentiated FReP cells exhibit minimal proliferation rates (FIG. 7) and c-MYC expression levels (FIG. 8*a*) in vitro and do not form teratoma in vivo (FIG. 6 and FIG. 12). It is noteworthy that TGF-β-stimulated SMAD signaling can directly upregulate $p15^{Ink4B}$ and $p21^{WAF1/Cip1}$ expression [40]. Thus, FMOD modulation of SMAD signaling may explain the increase of $p15^{Ink4B}$ and $p21^{WAF1/Cip1}$ in undifferentiated FReP cells (FIGS. 8*b* and *c*). Meanwhile, active SMAD suppression of c-MYC is essential for TGF-β induced cytostasis since c-MYC interacts directly with SMAD2/3 to block SMAD and SP1 dependent transcription oiP15Ink4B and p21WAF1/CiP1 [40]. Since low c-MYC and high $p15^{Ink4B}$ and $p21^{WAF1/Cip1}$ levels promote cytostasis [40], the expression profile of these genes in undifferentiated FReP cells may explain the absence of FReP-associated teratoma relative to undifferentiated iPS cells in which high c-MYC and low $p15^{Ink4B}$ and $p21^{WAF1/Cip1}$ conditions favor teratoma formation. However, further studies are needed to address the specific mechanism underlying cell reprogramming by this simple exposure to FMOD.

Remarkably, the slow proliferative rate of undifferentiated FReP cells is significantly reversed by culture in differentiation media, and differentiating FReP cells proliferate faster overall than differentiating iPS cells (FIG. 7). In addition, $p15^{Ink4B}$ and $p21^{WAF1/Cip1}$, which are critical in suppressing tumorigenesis and maintaining stem cell quiescence [79-82], are increased in undifferentiated FReP cells (FIGS. 8*b* and *c*). Phenotypically, concomitant molecular multipotency and cytostasis marker expression coupled with low proliferation rates (unless stimulated to differentiate) as seen in the FReP cells are more typical of quiescent stem cells than iPS cells that require induction of cell proliferation for reprogramming [26,37,40]. Moreover, the lack of teratoma formation by FReP cells suggests that from a tumor avoidance perspective, undifferentiated or partially differentiated FReP cells do not need to be selected out before in vivo therapeutic implantation. Since incompletely differentiated ES and iPS cells are known to be tumorigenic and have to be removed before implantation [44,83], this would make FReP cells potentially safer and less cumbersome than ES or iPS cells for clinical applications. Lastly, although the degree of dedifferentiation of FReP cells may not be as complete as that of other reported pluripotent stem cells at least with respect to proliferation and teratoma formation, FReP cells may be a safer and more easily applied method for clinical human tissue regeneration.

5. CONCLUSION

This study demonstrates that FMOD, a single ECM proteoglycan, can directly reprogram human fibroblasts to a minimally proliferative, multipotent state that resembles quiescent stem cells. Collectively, these results raise intriguing questions regarding FMOD's role in TGF-β/SMAD signaling and the molecular nexus governing cell reprogramming, stem cell quiescence, and tumorigenicity. Overall, additional detailed studies on FReP cell genetic stability, epigenetic memory, in vivo pluripotency, and long term viability are required. However, we believe that FMOD-based reprogramming may become a major enabling technology for cell-based therapies and tissue engineering applications due to its ease of application, non-integrative nature, and lack of teratoma formation.

REFERENCES

[1] Wilmut I, Schnieke A E, McWhir J, Kind A J, Campbell K H. Viable offspring derived from fetal and adult mammalian cells. Nature 1997; 385:810-3.

[2] Wakayama T, Perry A C, Zuccotti M, Johnson K R, Yanagimachi R. Full-term development of mice from enucleated oocytes injected with cumulus cell nuclei. Nature 1998; 394:369-74.

[3] Byme J A, Pedersen D A, Clepper L L, Nelson M, Sanger W G, Gokhale S, et al. Producing primate embryonic stem cells by somatic cell nuclear transfer. Nature 2007; 450: 497-502.

[4] Tada M, Takahama Y, Abe K, Nakatsuji N, Tada T. Nuclear reprogramming of somatic cells by in vitro hybridization with E S cells. Curr Biol 2001; 11:1553-8.

[5] Cowan C A, Atienza J, Melton D A, Eggan K. Nuclear reprogramming of somatic cells after fusion with human embryonic stem cells. Science 2005; 309: 1369-73.

[6] Takahashi K, Yamanaka S. Induction of pluripotent stem cells from mouse embryonic and adult fibroblast cultures by defined factors. Cell 2006; 126:663-76.

[7] Yu J, Vodyanik M A, Smuga-Otto K, Antosiewicz-Bourget J, Frane J L, Tian S, et al. Induced pluripotent stem cell lines derived from human somatic cells. Science 2007; 318:1917-20.

[8] Okita K, Ichisaka T, Yamanaka S. Generation of germline-competent induced pluripotent stem cells. Nature 2007; 448:313-7.

[9] Wemig M, Meissner A, Foreman R, Brambrink T, Ku M, Hochedlinger K, et al. In vitro reprogramming of fibroblasts into a pluripotent ES-cell-like state. Nature 2007; 448:318-24.

[10] Maherali N, Sridharan R, Xie W, Utikal J, Eminli S, Amold K, et al. Directly reprogrammed fibroblasts show global epigenetic remodeling and widespread tissue contribution. Cell Stem Cell 2007; 1:55-70.

[11] Warren L, Manos P D, Ahfeldt T, Loh Y H, Li H, Lau F, et al. Highly efficient reprogramming to pluripotency and directed differentiation of human cells with synthetic modified mRNA. Cell Stem Cell 2010; 7:618-30.

[12] Walia B, SatijaN, Tripathi R P, Gangenahalli G U. Induced pluripotent stem cells: fundamentals and applications of the reprogramming process and its ramifications on regenerative medicine. Stem Cell Rev Rep 2012; 8: 100-15.

[13] Miura K, Okada Y, Aoi T, Okada A, Takahashi K, Okita K, et al. Variation in the safety of induced pluripotent stem cell lines. Nat Biotechnol 2009; 27:743-5.

[14] Zheng Z, Nguyen C, Zhang X, Khorasani H, Wang J Z, Zara J N, et al. Delayed wound closure in fibromodulin-deficient mice is associated with increased TGF-beta3 signaling. J Invest Dermatol 2011; 131:769-78.

[15] Lowry W E, Richter L, Yachechko R, Pyle A D, Tchieu J, Sridharan R, et al. Generation of human induced pluripotent stem cells from dermal fibroblasts. Proc Natl Acad Sci USA 2008; 105:2883-8.

[16] Hotta A, Cheung A Y, Farra N, Vijayaragavan K, Seguin C A, Draper J S, et al. Isolation of human iPS cells using EOS lentiviral vectors to select for pluripotency. Nat Methods 2009; 6:370-6.

[17] Roy N S, Nakano T, Xuing L, Kang J, Nedergaard M, Goldman S A. Enhancer-specified GFP-based FACS purification of human spinal motor neurons from embryonic stem cells. Exp Neurol 2005; 196:224-34.

[18] Nizzardo M, Simone C, Falcone M, Locatelli F, Riboldi G, Comi G P, et al. Human motor neuron generation from embryonic stem cells and induced pluripotent stem cells. Cell Mol Life Sci 2010; 67:3837-47.

[19] Huangfu D, Osafune K, Maehr R, Guo W, Eijkelenboom A, Chen S, et al. Induction of pluripotent stem cells from primary human fibroblasts with only Oct4 and Sox2. Nat Biotechnol 2008; 26: 1269-75.

[20] DAmour K A, Agulnick A D, Eliazer S, Kelly O G, Kroon E, Baetge E E. Efficient differentiation of human embryonic stem cells to definitive endoderm. Nat Biotechnol 2005; 23: 1534-41.

[21] Zhang J, Wilson G F, Soerens A G, Koonce C H, Yu J, Palecek S P, et al. Functional cardiomyocytes derived from human induced pluripotent stem cells. Circ Res 2009; 104:e30-41.

[22] Crisan M, Yap S, Casteilla L, Chen C W, Corselli M, Park T S, et al. A perivascular origin for mesenchymal stem cells in multiple human organs. Cell Stem Cell 2008; 3:301-13.

[23] Zhang X, Peault B, Chen W, Li W, Corselli M, James A W, et al. The Nell-1 growth factor stimulates bone formation by purified human perivascular cells. Tissue Eng Part A 2011; 17:2497-509.

[24] Ausubel F M, Brent R, Kingston R E, More D D, Seidman J G, Smith J A, et al. Short protocols in molecular biology. 4th ed. New York: Wiley John & Sons Inc.; 1999.

[25] Villa-Diaz L G, Nandivada H, Ding J, Nogueira-de-Souza N C, Krebsbach P H,
O'Shea K S, et al. Synthetic polymer coatings for long-term growth of human embryonic stem cells. Nat Biotechnol 2010; 28:581-3.

[26] Papp B, Plath K. Reprogramming to pluripotency: stepwise resetting of the epigenetic landscape. Cell Res 2011; 21:486-501.

[27] Theunissen T W, Silva J C R. Switching on pluripotency: a perspective on the biological requirement of Nanog. Philos Trans R Soc Lond B Biol Sci 2011; 366:2222-9.

[28] Beattie G M, Lopez A D, Bucay N, Hinton A, Firpo M T, King C C, et al. Activin A maintains pluripotency of human embryonic stem cells in the absence of feeder layers. Stem Cells 2005; 23:489-95.

[29] Xu R H, Sampsell-Barron T L, Gu F, Root S, Peck R M, Pan G, et al. NANOG is a direct target of TGFbeta/activin-mediated SMAD signaling in human ESCs. Cell Stem Cell 2008; 3: 196-206.

[30] Besser D. Expression of nodal, lefty-a, and lefty-B in undifferentiated human embryonic stem cells requires activation of Smad2/3. J Biol Chem 2004; 279:45076-84.

[31] James D, Levine A J, Besser D, Hemmati-Brivanlou A. TGFbeta/activin/nodal signaling is necessary for the maintenance of pluripotency in human embryonic stem cells. Development 2005; 132: 1273-82.

[32] Vallier L, Alexander M, Pedersen R A. Activin/Nodal and FGF pathways cooperate to maintain pluripotency of human embryonic stem cells. J Cell Sci 2005; 118:4495-509.

[33] Xiao L, Yuan X, Sharkis S J. Activin A maintains self-renewal and regulates fibroblast growth factor, Wnt, and bone morphogenic protein pathways in human embryonic stem cells. Stem Cells 2006; 24: 1476-86.

[34] Fujita T, Azuma Y, Fukuyama R, Hattori Y, Yoshida C, Koida M, et al. Runx2 induces osteoblast and chondrocyte differentiation and enhances their migration by coupling with PI3K-Akt signaling. J Cell Biol 2004; 166:85-95.

[35] Shen J, Hovhannisyan H, Lian J B, Montecino M A, Stein G S, Stein J L, et al.
Transcriptional induction of the osteocalcin gene during osteoblast differentiation involves acetylation of histones h3 and h4. Mol Endocrinol 2003; 17:743-56.

[36] Yan Z, Choi S, Liu X, Zhang M, Schageman J J, Lee S Y, et al. Highly coordinated gene regulation in mouse skeletal muscle regeneration. J Biol Chem 2003; 278: 8826-36.

[37] Ruiz S, Panopoulos A D, Herrerias A, Bissig K D, Lutz M, Berggren W T, et al. A high proliferation rate is required for cell reprogramming and maintenance of human embryonic stem cell identity. Curr Biol 2011; 21:45-52.

[38] Schmidt E V. The role of c-myc in regulation of translation initiation. Oncogene 2004; 23:3217-21.

[39] Nakagawa M, Koyanagi M, Tanabe K, Takahashi K, Ichisaka T, Aoi T, et al. Generation of induced pluripotent stem cells without Myc from mouse and human fibroblasts. Nat Biotechnol 2008; 26: 101-6.

[40] Gold L, Lecanda J. Mechanisms of cell cycle regulation by TGF-0 disabled in cancer. In: Jakowlew S B, editor. Transforming growth factor-3 in cancer therapy. Totowa, N.J.: Humana Press Inc.; 2008.

[41] Li J Y, Christophersen N S, Hall V, Soulet D, Brundin P. Critical issues of clinical human embryonic stem cell therapy for brain repair. Trends Neurosci 2008; 31: 146-53.

[42] Yamanaka S. Strategies and new developments in the generation of patient-specific pluripotent stem cells. Cell Stem Cell 2007; 1:39-49.

[43] Wernig M, Zhao J P, Pruszak J, Hedlund E, Fu D, Soldner F, et al. Neurons derived from reprogrammed fibroblasts functionally integrate into the fetal brain and improve symptoms of rats with Parkinson's disease. Proc Natl Acad Sci USA 2008; 105:5856-61.

[44] Yamanaka S. A fresh look at iPS cells. Cell 2009; 137: 13-7.

[45] Stadtfeld M, Nagaya M, Utikal J, Weir G, Hochedlinger K. Induced pluripotent stem cells generated without viral integration. Science 2008; 322:945-9.

[46] Okita K, Nakagawa M, Hyenjong H, Ichisaka T, Yamanaka S. Generation of mouse induced pluripotent stem cells without viral vectors. Science 2008; 322:949-53.

[47] Barrilleaux B, Knoepfier P S. Inducing iPSCs to escape the dish. Cell Stem Cell 2011; 9: 103-11.

[48] Ellis J, Bruneau B G, Keller G, Lemischka I R, Nagy A, Rossant J, et al. Alternative induced pluripotent stem cell characterization criteria for in vitro applications. Cell Stem Cell 2009; 4: 198-9.

[49] Fox X L. Human iPSC and ESC translation potential debated. Nat Biotechnol 2011; 29:375-6.

[50] Zhou Q, Brown J, Kanarek A, Rajagopal J, Melton D A. In vivo reprogramming of adult pancreatic exocrine cells to beta-cells. Nature 2008; 455:627-32.
[51] Vierbuchen T, Ostermeier A, Pang Z P, Kokubu Y, Sudhof T C, Wernig M. Direct conversion of fibroblasts to functional neurons by defined factors. Nature 2010; 463: 1035-41.
[52] Taranger C K, Noer A, Sorensen A L, Hakelien A M, Boquest A C, Collas P. Induction of dedifferentiation, genomewide transcriptional programming, and epigenetic reprogramming by extracts of carcinoma and embryonic stem cells. Mol Biol Cell 2005; 16:5719-35.
[53] Hansis C, Barreto G, Maltry N, Niehrs C. Nuclear reprogramming of human somatic cells by xenopus egg extract requires BRG1. Curr Biol 2004; 14:1475-80.
[54] Zhu X Q, Pan X H, Wang W, Chen Q, Pang R Q, Cai X M, et al. Transient in vitro epigenetic reprogramming of skin fibroblasts into multipotent cells. Biomaterials 2010; 31:2779-87.
[55] Ng V Y, Choo A B H. iPS and E S cells: do both roads lead to Rome? The Open Stem Cell Journal 2010; 2:8-17.
[56] Cavaleri F, Scholer H R. Nanog: a new recruit to the embryonic stem cell orchestra. Cell 2003; 113:551-2.
[57] Chambers I, Colby D, Robertson M, Nichols J, Lee S, Tweedie S, et al. Functional expression cloning of Nanog, a pluripotency sustaining factor in embryonic stem cells. Cell 2003; 113:643-55.
[58] Mitsui K, Tokuzawa Y, Itoh H, Segawa K, Murakami M, Takahashi K, et al. The homeoprotein Nanog is required for maintenance of pluripotency in mouse epiblast and E S cells. Cell 2003; 113:631-42.
[59] Boyer L A, Lee T I, Cole M F, Johnstone S E, Levine S S, Zucker J P, et al. Core transcriptional regulatory circuitry in human embryonic stem cells. Cell 2005; 122:947-56.
[60] Loh Y H, Wu Q, Chew J L, Vega V B, Zhang W, Chen X, et al. The Oct4 and Nanog transcription network regulates pluripotency in mouse embryonic stem cells. Nat Genet 2006; 38:431-40.
[61] Kim J, Chu J, Shen X, Wang J, Orkin S H. An extended transcriptional network for pluripotency of embryonic stem cells. Cell 2008; 132:1049-61.
[62] Jiang Y, Jahagirdar B N, Reinhardt R L, Schwartz R E, Keene C D, Ortiz-Gonzalez X R, et al. Pluripotency of mesenchymal stem cells derived from adult marrow. Nature 2002; 418:41-9.
[63] Pittenger M F, Mackay A M, Beck S C, Jaiswal R K, Douglas R, Mosca J D, et al. Multilineage potential of adult human mesenchymal stem cells. Science 1999; 284: 143-7.
[64] Woodbury D, Reynolds K, Black I B. Adult bone marrow stromal stem cells express germline, ectodermal, endodermal, and mesodermal genes prior to neurogenesis. J Neurosci Res 2002; 69:908-17.
[65] Zuk P A, Zhu M, Mizuno H, Huang J, Futrell J W, Katz A J, et al. Multilineage cells from human adipose tissue: implications for cell-based therapies. Tissue Eng 2001; 7:211-28.
[66] Bi Y, Ehirchiou D, Kilts™, Inkson C A, Embree M C, Sonoyama W, et al. Identification of tendon stem/progenitor cells and the role of the extracellular matrix in their niche. Nat Med 2007; 13: 1219-27.
[67] Radtke S, Horn P A. Cells, niche, fate: meeting report on the 6th International Meeting of the Stem Cell Network North Rhine Westphalia. Cell reprogram 2011; 13:381-4.
[68] Eshghi S, Schaffer D V. Engineering microenvironments to control stem cell fate and function. In: The Stem Cell Research Community, editors. StemBook. Cambridge, Mass.: Harvard Stem Cell Institute; 2008.
[69] Zheng Z, Nguyen K, Wang J Z, Zhang X, Ting K, Soo C. Differential expression of transforming growth factor (TGF)-P s and TGF-β receptors during skin wound healing in adult mice with fibromodulin (FMOD) deficiency. Wound Repair Regen 2008; 16:A28-A.
[70] Khorasani H, Zheng Z, Nguyen C, Zara J, Zhang X L, Wang J C, et al. A quantitative approach to scar analysis. Am J Pathol 2011; 178:621-8.
[71] Sjoberg A, Onnerfjord P, Morgelin M, Heinegard D, Blom A M. The extracellular matrix and inflammation: fibromodulin activates the classical pathway of complement by directly binding Clq. J Biol Chem 2005; 280: 32301-8.
[72] Sjoberg A P, Manderson G A, Morgelin M, Day A J, Heinegard D, Blom A M. Short leucine-rich glycoproteins of the extracellular matrix display diverse patterns of complement interaction and activation. Mol Immunol 2009; 46:830-9.
[73] Mayr C, Bund D, Schlee M, Moosmann A, Kofier D M, Hallek M, et al. Fibromodulin as a novel tumor-associated antigen (TAA) in chronic lymphocytic leukemia (CLL), which allows expansion of specific CD8+ autologous T lymphocytes. Blood 2005; 105: 1566-73.
[74] Svensson L, Aszodi A, Reinholt F P, Fassler R, Heinegard D, Oldberg A. Fibromodulin-null mice have abnormal collagen fibrils, tissue organization, and altered lumican deposition in tendon. J Biol Chem 1999; 274:9636-47.
[75] Oldberg A, Kalamajski S, Salnikov A V, Stuhr L, Morgelin M, Reed R K, et al. Collagen-binding proteoglycan fibromodulin can determine stroma matrix structure and fluid balance in experimental carcinoma. Proc Natl Acad Sci USA 2007; 104: 13966-71.
[76] Ichida J K, Blanchard J, Lam K, Son E Y, Chung J E, Egli D, et al. A small-molecule inhibitor of tgf-Beta signaling replaces sox2 in reprogramming by inducing nanog. Cell Stem Cell 2009; 5:491-503.
[77] Theunissen T W, van Oosten A L, Caste lo-Branco G, Hall J, Smith A, Silva J C R. Nanog overcomes reprogramming barriers and induces pluripotency in minimal conditions. Curr Biol 2011; 21:65-71.
[78] Lin T X, Ambasudhan R, Yuan X, Li W L, Hilcove S, Abujarour R, et al. A chemical platform for improved induction of human iPSCs. Nat Methods 2009; 6:805-U24.
[79] Ruscetti F W, Bartelmez S H. Cell cycle control and check points in hematopoietic stem cells. In: Lanza R, Gearhart J, Hogan B, Melton D, Pedersen R, Thomson J, et al, editors. Handbook of stem cells. San Diego: Elsevier Academic Press; 2004.
[80] Kippin T E, Martens D J, van der Kooy D. p21 loss compromises the relative quiescence of forebrain stem cell proliferation leading to exhaustion of their proliferation capacity. Genes Dev 2005; 19:756-67.
[81] Cheng T, Rodrigues N, Shen H, Yang Y, Dombkowski D, Sykes M, et al. Hematopoietic stem cell quiescence maintained by p21cip1/waf1. Science 2000; 287: 1804-8.
[82] Cheng T. Cell cycle inhibitors in normal and tumor stem cells. Oncogene 2004; 23:7256-66.
[83] Bilousova G, Jun D H, King K B, De Langhe S, Chick W S, Torchia E C, et al. Osteoblasts derived from induced pluripotent stem cells form calcified structures in scaffolds both in vitro and in vivo. Stem Cells 2011; 29:206-16.

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

We claim:

1. A method of pluripotency reprogramming, comprising:

treating a human cell with a cell culture medium comprising fibromodulin (FMOD) for a period ranging from a day to a month, and changing the cell culture medium regularly until a FMOD reprogrammed (FreP) cell forms;

wherein the FreP cell expresses NANOG and does not form teratoma, and wherein the human cell is a fibroblastic cell.

2. The method according to claim 1, wherein the FMOD has a concentration from about 200 nM to about 800 nM.

3. The method according to claim 1, wherein the human cell is a BJ fibroblast or primary adult normal human dermal fibroblast (NHDF).

* * * * *